US006458590B1

(12) United States Patent
Mukherjee et al.

(10) Patent No.: US 6,458,590 B1
(45) Date of Patent: Oct. 1, 2002

(54) METHODS AND COMPOSITIONS FOR TREATMENT OF RESTENOSIS

(75) Inventors: Anil B. Mukherjee, Brookeville, MD (US); Gopal C. Kundu, Maharashtra (IN); Dibyendu K. Panda, Montreal (CA)

(73) Assignee: The United States of America, as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/485,077

(22) PCT Filed: Aug. 7, 1998

(86) PCT No.: PCT/US98/16569

§ 371 (c)(1),
(2), (4) Date: Jun. 23, 2000

(87) PCT Pub. No.: WO99/07844

PCT Pub. Date: Feb. 18, 1999

Related U.S. Application Data

(60) Provisional application No. 60/054,967, filed on Aug. 7, 1997.

(51) Int. Cl.$^7$ .......................... C12Q 1/68; C07H 21/04; C12N 15/85
(52) U.S. Cl. ...................... 435/375; 436/91.1; 436/325; 436/366; 536/23.1; 536/24.31; 536/24.33; 536/245
(58) Field of Search ............................. 514/44; 435/6, 435/325, 366, 375, 91.1; 536/23.1, 24.5, 25.3

(56) References Cited

U.S. PATENT DOCUMENTS

| | | |
|---|---|---|
| 4,512,762 A | 4/1985 | Spears |
| 4,824,436 A | 4/1989 | Wolinsky |
| 4,929,602 A | 5/1990 | Harker et al. |
| 5,417,978 A | 5/1995 | Tari et al. |
| 5,801,154 A * | 9/1998 | Baracchini et al. ........... 514/44 |

FOREIGN PATENT DOCUMENTS

| | | |
|---|---|---|
| WO | WO 94/26888 | 5/1994 |

OTHER PUBLICATIONS

Goran Andersson et al., Adhesion of Human Myelomonecydtic (HL–60) Cells Induced by 1,25–dihydroxyvitamin D3 and Phorbol Myristate Acetate is Dependent on Osteopontin Synthesis and the Integrin, Connective Tissue Research, vol. 35, pp. 163–171.*
Andrea S. Weintraub et al., Autocrine Secretion of Osteopontin by Vascular Smooth Muscle Cells Regulates Their Adhesion to Collagen Gels, American Journal of Pathology, vol. 1–19, No. 1, pp. 259–272.*
Mark K. Hirko et al., Antisense oligonucleotides against FGFR–1, Tenascin, and osteopontin inhibit Canine vein graft myointimal hyperplasia, Vascular, pp. 349–351.*
W. Michael Flanagan et al., Cellular penetration and antisense activity by a phenoxazine–substituted heptanucleotide Research.*
Andrea D. Branch, A good antisense molecule is hard to find, TIBS 23—Feb. 1998, pp. 45–50.*
Austin et al., "Intimal Proliferation of Smooth Muscle Cells as an Explanation for Recurrent Coronary Artery Stenosis after Percutaneous Translumial Coronary Angioplasty," J. Am. Coll. Cardiol. 6:369–375 (1985).
Chacklaparampil et al., "Cells in vivo and in vitro from osteopetrotic mice homozygous for c–src disruption show suppression of synthesis of osteopontin, a multifunctional extracellular matrix protein," Oncogene 12:1457–1467 (1996).
Chomcznski et al., "Single–Step Method of RNA Isolation by Acid Guanidinium Thiocyanate–Phenol–Chloroform Extraction," Anal. Biochem. 162:156–159 (1987).
Coombs, *Dictionary of Biotechnology* Stockton Press, New York, New York (1994) (Title and Copyright Pages Only).
Craig et al., "Secreted Phosphoprotein mRNA is Induced during Multi–stage Carcinogenesis in Mouse Skin and Correlates with the Metastatic Potential of Murine Fibroblasts," Int. J. Cancer 46:133–137 (1989).
Denhardt et al., "Osteopontin: a protein with diverse functions," FASEB J. 7:1473–1482 (1993).
Dzau et al., "Gene therapy for cardiovascular disease," Trends Biotechnol. 11:205–210 (1993).
Edelman et al., "Basic Fibroblast Growth Factor Enhances the Coupling of Intimal Hyperplasia and Proliferation of Vasa Vasorum in Injured Rat Arteries," J. Clin. Invest 89:465–473 (1992).
Ferrell et al., "A Deilemma for the 1990s, Choosing Appropriate Experimental Animal Model for the Prevention of Restenosis," Circulation 85:1630–1631 (1992).
Flugelman et al., "Low Level In Vivo Gene Transfer into the Arterial Wall Through a Perforated Balloon Catheter," Circulation 85:1110–1117 (1992).

(List continued on next page.)

Primary Examiner—Sean McGarry
Assistant Examiner—M Schmidt
(74) Attorney, Agent, or Firm—Medlen & Carroll, LLP

(57) ABSTRACT

The present invention provides sequences capable of inhibiting osteopontin (OPN) expression. In particular, the sequences provided herein are antisense osteopontin oligonucleotide sequences. The present invention further provides methods for treating restenosis using antisense osteopontin oligonucleotide sequences. In particular, methods for treating restenosis following vascular surgery (e.g., percutaneous transluminal coronary angioplasty (PCTA) and directional coronary atherectomy (DCA)) by using antisense osteopontin oligonucleotide sequences are provided.

7 Claims, 9 Drawing Sheets

OTHER PUBLICATIONS

Franzen et al., "Isolation and characterization of two sialoproteins present only in bone calcified matrix," Biochem. J 232:715–724 (1985).

Gadeau et al., "Osteopontin Overexpression is Associated with Arterial Smooth Muscle Cell Proliferation In Vitro," Arteriosclerosis & Thrombosis 13:120–125 (1993).

Giachelli et al., Molecular Cloning and Characterization of 2B7, a Rat mRNA which Distinguishes Smooth Muscle Cell Phenotypes in Vitro and is Identical to Osteopontin (Secreted Phosphoprotein I, 2aR) Biochem. Biophys. Res. Commun. 177:867–873 (1991).

Giachelli et al., "Osteopontin is Elevated during Neointima Formation in Rat Arteries and is a Novel Component of Human Atherscletoric Plaques," J. Clin. Invest. 92:1686–1696 (1993).

Giraldo et al., "Intimal Hyperplasia as a Cause of Restenosis After Percutaneous Transluminal Coronary Angioplasty," Arch. Pathol. Lab. Med. 109:173–175 (1985).

Hajjar et al., "Atherosclerosis," Amer. Scientist 83:460–467 (1995).

Hunter et al., "Preparation of Iodine–131 Labelled Human Growth Hormone of High Specific Activity," Nature 194:495–496 (1962).

Hynes, "Integrins: Versatility, Modulation, and Signaling in Cell Adhesion," Cell 69:11–25 (1992).

Ikeda et al., "Osteopontin mRNA is Expressed by Smooth Muscle–derived Foam Cells in Human Atherosclerotic Lesions of the Aorta," J. Clin. Invest. 92:2814–2820 (1993).

Kaneda et al., "Increased Expression of DNA Cointroduced with Nuclear Protein in Adult Rat Liver," Science 243:375–378 (1989).

Kiefer et al., "The cDNA and derived amino acid sequence for human osteopontin," Nucleic acids Res. 17:3306 (1989).

Kubota et al., "Influence of an Intemittent Compressive Force on Matrix Protein Expression by ROS 17/2.8 Cells, with Selective Stimulation of Osteopontin," Archs. Oral Biol. 38:23–30 (1993).

Kundu et al., "Recombinant human uteroglobin suppresses cellular invasiveness via a novel class of high–affinity cell surface binding site," Proc. Natl. Acad. Sci. USA 93:2915–2919 (1996).

Laemmli et al., "Cleavage of Structural Proteins during the Assembly of the Head of Bacteriophage T4," Nature 227:680–685 (1970).

Lee et al., "In Vivo Adenoviral Vector–Mediated Gene Transfer into Balloon–Injured Rat Carotid Arteries," Circ. Res. 73:797–807 (1993).

Lemarchand et al., "In Vivo Gene Transfer and Expression in Normal Uninjured Blood Vessels Using Replication–Deficient Recombinant Adenovirus Vectors," Circ. Res. 72:1132–1138 (1993).

Liaw et al., "Osteopontin promotes vascular cell adhesion and spreading and is chemotactic for smooth muscle cells in vitro," Circ. Res. 74:214–224 (1994).

Liaw et al., "The Adhesive and Migratory Effects of Osteopontin Are Mediated via Distinct Cell Surface Integrins," J. Clin. Invest. 95:713–724 (1995).

Lim et al., "Direct In Vivo Gene Transfer Into the Coronary Peripheral Vasculatures of the Intact Dog," Circulation 83:2007–2011 (1991).

Lynch et al., "Long–Term Expression of Human Adenosine Deaminase in Vascular Smooth Muscle Cells of Rats: A Model for Gene Therapy," Proc. Natl. Acad. Sci. USA 89:1138–1142 (1992).

Miller et al., "Gene Transfer by Retrovirus Vectors Occurs Only in Cells that are Actively Replicating at the Time of Infection," Mol. Cell Biol. 10:4239–4242 (1990).

Monfardini et al., "Recombinant Antibodies in Bioactive Peptide Design," J. Biol. Chem. 270:6628–6638 (1995).

Morishita et al., "Single Intraluminal Delivery of Antisense cdc2Kinase and Proliferating–Cell Nuclear Antigen Oligonucleotides Results in Chronic Inhibition of Neointimal Hyperplasia," Proc. Natl. Acad. Sci. USA 90:8474–8478 (1993).

Morishita et al., "Novel and Effective Gene Transfer Technique for Study of Vascular Renin Angiotensin System," J. Clin. Invest. 91:2580–2585 (1993).

Munson et al., "Ligand: A Versatile Computerized Approach for Characterization of Ligand–Binding Systems," Anal. Biochem. 107:220–239 (1980).

Nabel et al., "Recombinant Gene Expresion in Vivo Within Endothelial Cells of the Arterial Wall," Science 244:1285–1288 (1990).

Naito et al., "Vitronectin–Induced Haptotaxis of Vascular Smooth Muscle Cells in Vitro," Exp. Cell Res. 194:154–156 (1991).

Naldini et al., "In Vivo Gene Delivery and Stable Transduction of Nondividing Cell by a Lentiviral Vector," Science 272:263–267 (1996).

Naldini et al., "Efficient transfer, integration, and sustained long–term expression of the transgene in adult rat brains injected with a lentiviral vector," Proc. Natl. Acad. Sci. USA 93:11382–11388 (1996).

Nemir et al., "Normal Rat Kidney Cells Secrete Both Phosphorylated and Nonphosphorylated Forms of Osteopontin Showing Different Physiological Properties," J. Biol. Chem. 264:18202–18208 (1989)

Oldberg et al., "Identification of a Bone Sialoprotein Receptor in Osteosarcoma Cells," J. Biol. Chem. 263:19433–19436 (1988).

Oldberg et al., "Cloning and sequence analysis of rat bone sialoprotein (osteopontin) cDNA reveals an Arg–Gly–Asp cell–binding sequence," Proc. Natl. Acad. Sci. USA 83:8819–8823 (1986).

Peri et al., "Expression of Clara Cell 10–kD Gene in the Human Endometrium and Its Relationship to Ovarian Menstrual Cycle," DNA and Cell Biol. 13:495–503 (1994).

Peri et al., "Tissue–specific Expression of the Gene Coding for Human Clara Cell 10–kD Protein, a Phospholipase $A_2$–inhibitory Protein," J. Clin. Invest. 92:2099–2109 (1993).

Peri et al., "Uteroglobin Gene Expression in the Rabbit Uterus throughout Gestation and in the Fetal Lung," J. Clin. Invest. 96:343–353 (1995).

Rodan, Annals New York Acad. Sci., pp. 1–5 (1994) This reference is not currently available; should the Examiner desire a copy, please let Applicants know so that one may be provided.

Ross, "The pathogenesis of atherosclerosis: a perspective for the 1990s," Nature 362:801–809 (1993).

Senger et al., "Transformed Mammalian Cells Secrete Specific Proteins and Phosphoproteins," Cell 16:885–893 (1979).

Senger et al., "Stimulation of Endothelial Cell Migration by Vascular Permeability Factor/Vascular Endothelial Growth Factor through Cooperative Mechanisms Involving the $\alpha_v\beta_3$ Integrin, Osteopontin, and Thrombin," Am. J. Pathol. 149:293–305 (1996).

Senger et al., "Secreted Phosphoproteins Associated with Neoplastic Transformation: Close Homology with Plasma Proteins Cleaved during Blood Coagulation," Cancer Res. 48:5770–5774 (1988).

Shanahan et al., "High Expression of Genes for Calcification-regulating Proteins in Human Atherosclerotic Plaques," J. Clin. Invest. 93:2393–2402 (1994).

Simons et al., "Antisense c–myb oligonucleotides inhibit intimal arterial smooth muscle cell accumulation in vivo," Nature 359:67–70 (1992).

Singh et al., "Physiological Properties and Differential Glycosylation of Phosphorylated and Nonphosphorylated Forms of Osteopontin Secreted by Normal Rat Kidney Cells," J. Biol. Chem. 265:18696–18701 (1990).

Singh et al., "Differential processing of osteopontin transcripts in rat kidney– and osteoblast–derived cell lines." J Biol Chem. 267(33):23847–51 (1992).

von der Leyen et al., "In Vivo Gene Transfer to Prevent Neointima Hyperplasia after Vascular Injury: Effect of Overexpression of Constitutive Nitric Oxide Synthase," FASEB J. 8:A802 (1994).

Wilson et al., "Implantation of Vascular Grafts Lined with Genetically Modified Endothelial Cells," Science 244:1344–1346 (1989).

Yue et al., "Osteopontin–Stimulated Vascular Smooth Muscle Cell Migration Is Mediated by $\beta_3$ Integrin," Exp. Cell Res. 214:459–464 (1994).

Andersson et al., "Adhesion of human myelomonocytic (HL–60) cells induced by 1,25–dihydroxyvitamin $D_3$ and phorbol myristate acetate is dependent on osteopontin synthesis and the alpha v beta 3 integrin," Connect Tissue Res. 35:163–171 (1996, Abstract only).

Branch, "A good antisense molecule is hard to find," TIBS, pp. 45–50 (Feb. 1998).

Hirko et al., "Antisense Oligonucleotides Against FGFR–1, Tenascin, and Osteopontin Inhibit Canine Vein Graft Myiontimal Hyperplasia," Surgical Forum 46:349–351 (1995).

Liaw et al., "Neutralizing antibodies directed against osteopontin inhibit rat carotid neointimal thickening after endothelial denudation," Arteriosclerosis, Thrombosis and Vascular Biology 17:188–193 (Jan. 1997).

Kundu et al., "Genetic predictors of coronary restenosis: Potential roles of osteopontin and its receptor gene expression in coronary restenosis after antioplasty," Am. J. Human Genet. 61:A312 (Suppl) (Oct. 1997).

Panda et al., "Potential roles of osteopontin and $\alpha_v\beta_3$ integrin in the development of coronary artery restenosis after angioplasty," Proc. Natl. Acad. Sci. USA 94:9308–9313 [1997].

* cited by examiner

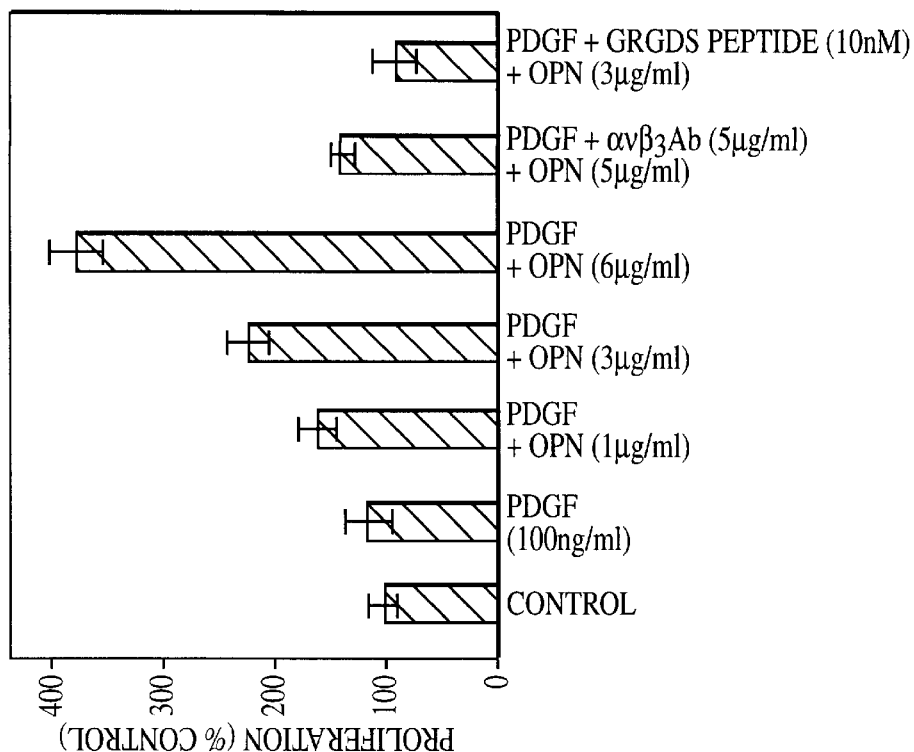
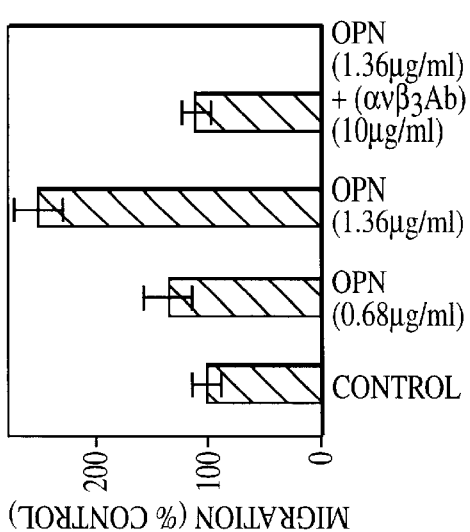
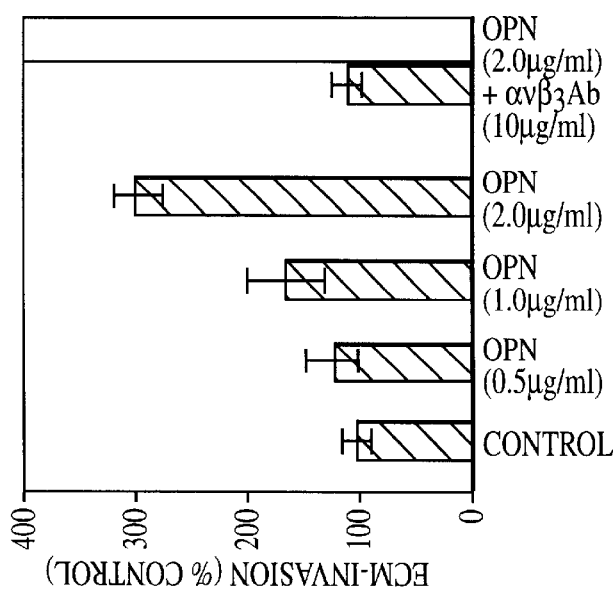
FIG. 2C
FIG. 2A
FIG. 2B

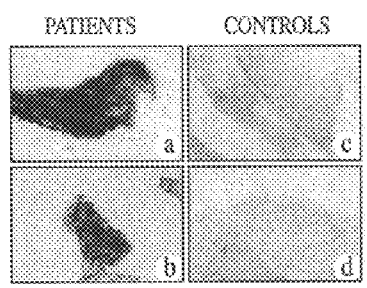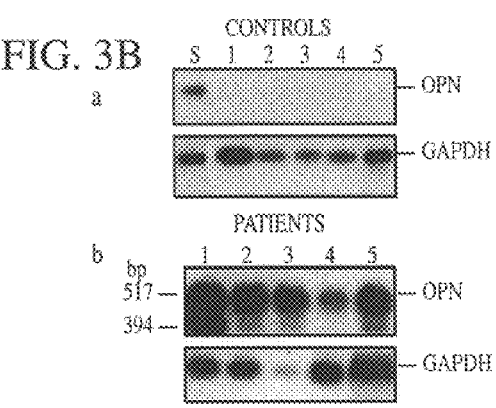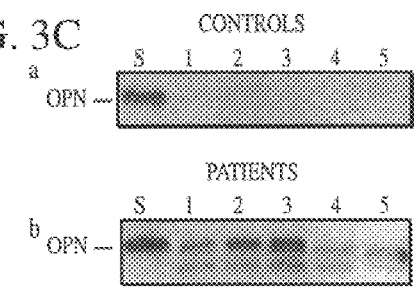

FIGURE 5

```
GACCAGACTC GTCTCAGGCC AGTTGCAGCC TTCTCAGCCA AACSCCGACC
AAGGAAAACT CACTACCATG AGAATTGCAG TGATTTGCTT TTGCCTCCTA
GGCATCACCT GTGCCATACC AGTTAAACAG GCTGATTCTG GAAGTTCTGA
GGAAAAGCAG CTTTACAACA AATACCCAGA TGCTGTGGCC ACATGGCTAA
ACCCTGACCC ATCTCAGAAG CAGAATCTCC TAGCCCCACA GAATGCTGTG
TCCTCTGAAG AAACCAATGA CTTTAAACAA GAGACCCTTC CAAGTAAGTC
CAACGAAAGC CATGACCACA TGGATGATAT GGATGATGAA GATGATGATG
ACCATGTGGA CAGCCAGGAC TCCATTGACT CGAACGACTC TGATGATGTA
GATGACACTG ATGATTCTCA CCAGTCTGAT GAGTCTCACC ATTCTGATGA
ATCTGATGAA CTGGTCACTG ATTTTCCCAC GGACCTGCCA GCAACCGAAG
TTTTCACTCC AGTTGTCCCC ACAGTAGACA CATATGATGG CCGAGGTGAT
AGTGTGGTTT ATGGACTGAG GTCAAAATCT AAGAAGTTTC GCAGACCTGA
CATCCAGTAC CCTGATGCTA CAGACGAGGA CATCACCTCA CACATGGAAA
GCGAGGAGTT GAATGGTGCA TACAAGGCCA TCCCCGTTGC CCAGGACCTG
AACGCGCCTT CTGATTGGGA CAGCCGTGGG AAGGACAGTT ATGAAACGAG
TCAGCTGGAT GACCAGAGTG CTGAAACCCA CAGCCACAAG CAGTCCAGAT
TATATAAGCG GAAAGCCAAT GATGAGAGCA ATGAGCATTC CGATGTGATT
GATAGTCAGG AACTTTCCAA AGTCAGCCGT GAATTCCACA GCCATGAATT
TCACAGCCAT GAAGATATGC TGGTTGTAGA CCCCAAAAGT AAGGAAGAAG
ATAAACACCT GAAATTTCGT ATTTCTCATG AATTAGATAG TGCATCTTCT
GAGGTCAATT AAAAGGAGAA AAAATACAAT TTCTCACTTT GCATTTAGTC
AAAAGAAAAA ATGCTTTATA GCAAATGAA AGAGAACATG AAATGCTTCT
TTCTCAGTTT ATTGGTTGAA TGTGTATCTA TTTGAGTCTG GAAATAACTA
ATGTGTTTGA TAATTAGTTT AGTTGTGGC TTCATGGAAA CTCCCTGTAA
ACTAAAAGCT TCAGGGTTAT GTCTATGTTC ATTCTATAGA AGAAATGCAA
ACTATCACTG TATTTAATA TTTGTTATTC TCTCATGAAT AGAAATTTAT
GTAGAAGCAA ACAAATACT TTTACCCACT TAAAAAGAGA ATATAACATT
TTATGTCACT ATAATCTTTT GTTTTTTAAG TTAGTGTATA TTTTGTTGTG
ATTATCTTTT TGTGGTGTGA ATAA
```

Figure 8

```
GCAAGCCTCA GCATCCTTGG CTTTGCAGTC TCCTGCGGCA AGCATTCTCG AGGAAGCCAG                    60

CCAAGGACCA ACTACAACC ATG AGA CTG GCA GTG GTT TGC CTT TGC CTG TTC                    112
                     Met Arg Leu Ala Val Val Cys Leu Cys Leu Phe
                      1           5                      10

GGC CTT GCC TCC TGT CTC CCG GTG AAA GTG GCT GAG TTT GGC AGC TCA                     160
Gly Leu Ala Ser Cys Leu Pro Val Lys Val Ala Glu Phe Gly Ser Ser
             15              20                  25

GAG GAG AAG GCG CAT TAC AGC AAA CAC TCA GAT GCT GTA GCC ACT TGG                     208
Glu Glu Lys Ala His Tyr Ser Lys His Ser Asp Ala Val Ala Thr Trp
         30              35              40

CTG AAG CCT GAC CCA TCT CAG AAG CAG AAT CTT CTA GCC CCA CAG AAT                     256
Leu Lys Pro Asp Pro Ser Gln Lys Gln Asn Leu Leu Ala Pro Gln Asn
     45              50              55

TCT GTG TCC TCT GAA GAA ACG GAT GAC TTT AAG CAA GAA ACT CTT CCA                     304
Ser Val Ser Ser Glu Glu Thr Asp Asp Phe Lys Gln Glu Thr Leu Pro
60              65              70                  75

AGC AAC TCC AAT GAA AGC CAT GAC CAC ATG GAC GAT GAT GAC GAC GAC                     352
Ser Asn Ser Asn Glu Ser His Asp His Met Asp Asp Asp Asp Asp Asp
                 80              85                  90

GAT GAC GAC GGA GAC CAT GCA GAG AGC GAG GAT TCT GTG AAC TCG GAT                     400
Asp Asp Asp Gly Asp His Ala Glu Ser Glu Asp Ser Val Asn Ser Asp
             95              100             105

GAA TCT GAC GAA TCT CAC CAT TCC GAT GAA TCT GAT GAG TCC TTC ACT                     448
Glu Ser Asp Glu Ser His His Ser Asp Glu Ser Asp Glu Ser Phe Thr
         110             115             120

GCC AGC ACA CAA GCA GAC GTT TTG ACT CCA ATC GCC CCC ACA GTC GAT                     496
Ala Ser Thr Gln Ala Asp Val Leu Thr Pro Ile Ala Pro Thr Val Asp
     125             130             135

GTC CCT GAC GGC CGA GGT GAT AGC TTG GCT TAC GGA CTG AGG TCA AAG                     544
Val Pro Asp Gly Arg Gly Asp Ser Leu Ala Tyr Gly Leu Arg Ser Lys
140             145             150             155

TCC AGG AGT TTC CCT GTT TCT GAT GAA CAG TAT CCC GAT GCC ACA GAT                     592
Ser Arg Ser Phe Pro Val Ser Asp Glu Gln Tyr Pro Asp Ala Thr Asp
                 160             165             170

GAG GAC CTC ACC TCC CGC ATG AAG AGC CAG GAG TCC GAT GAG GCT ATC                     640
Glu Asp Leu Thr Ser Arg Met Lys Ser Gln Glu Ser Asp Glu Ala Ile
             175             180             185

AAG GTC ATC CCA GTT GCC CAG CGT CTG AGC GTG CCC TCT GAT CAG GAC                     688
Lys Val Ile Pro Val Ala Gln Arg Leu Ser Val Pro Ser Asp Gln Asp
         190             195             200

AGC AAC GGG AAG ACC AGC CAT GAG TCA AGT CAG CTG GAT GAA CCA AGC                     736
Ser Asn Gly Lys Thr Ser His Glu Ser Ser Gln Leu Asp Glu Pro Ser
     205             210             215

GTG GAA ACA CAC AGC CTG GAG CAG TCC AAG GAG TAT AAG CAG AGG GCC                     784
Val Glu Thr His Ser Leu Glu Gln Ser Lys Glu Tyr Lys Gln Arg Ala
220             225             230             235
```

Figure 8 (Continued)

```
AGC CAC GAG AGC ACT GAG CAG TCG GAT GCG ATC GAT AGT GCC GAG AAG    832
Ser His Glu Ser Thr Glu Gln Ser Asp Ala Ile Asp Ser Ala Glu Lys
            240             245             250

CCG GAT GCA ATC GAT AGT GCA GAG CGG TCG GAT GCT ATC GAC AGT CAG    880
Pro Asp Ala Ile Asp Ser Ala Glu Arg Ser Asp Ala Ile Asp Ser Gln
            255             260             265

GCG AGT TCC AAA GCC AGC CTG GAA CAT CAG AGC CAC GAG TTT CAC AGC    928
Ala Ser Ser Lys Ala Ser Leu Glu His Gln Ser His Glu Phe His Ser
            270             275             280

CAT GAG GAC AAG CTA GTC CTA GAC CCT AAG AGT AAG GAA GAT GAT AGG    976
His Glu Asp Lys Leu Val Leu Asp Pro Lys Ser Lys Glu Asp Asp Arg
            285             290             295

TAT CTG AAA TTC CGC ATT TCT CAT GAA TTA GAG AGT TCA TCT TCT GAG   1024
Tyr Leu Lys Phe Arg Ile Ser His Glu Leu Glu Ser Ser Ser Ser Glu
300             305             310             315

GTC AAT TAAAGAAGAG GCAAAACCAC AGTTCCTTAC TTTGCTTTAA ATAAAACAAA    1080
Val Asn

AAGTAAATTC CAACAAGCAG GAATACTAAC TGCTTGTTTC TCAGTTCAGT GGATACATGT  1140

ATGTGGACAA AGAAATAGAT AGTGTTTTGG GCCCTGAGCT TAGTTCGTTG TTTCATGCAG  1200

ACACCACTGT AACCTAGAAG TTTCAGCATT TCGCTTCTGT TCTTTCTGTG CAAGAAATGC  1260

AAATGGCCAC TGCATTTTAA TGATTGCTAT TCTTTTATGA ATAAAATGTA TGTAGAGGCA  1320

GGCAAACTTA CAGGAACAGC AAAATTAAAA GAGAAACTAT AATAGTCTGT GTCACTATAA  1380

TCTTTTGGTT TTATAATTAG TGTATATTTT GTTGTGATTA TTTTTGTTGG TGTGAATAAA  1440

TCTTGTATCT TGAATGTAAA AAAAAAAAA AAA                               1473
```

METHODS AND COMPOSITIONS FOR TREATMENT OF RESTENOSIS

This application claims the benefit of U.S. Provisional Application No. 60/054,967, filed Aug. 7, 1997, and is a National Stage entry under 35 U.S.C. 371 of International Patent Application PCT/US98/16569, filed Aug. 7, 1998.

This work was made with Government support by the National Institutes of Health. The Government has certain rights in this invention.

FIELD OF THE INVENTION

The present invention provides sequences capable of inhibiting osteopontin (OPN) expression. In particular, the sequences provided herein are antisense osteopontin oligonucleotide sequences. The present invention further relates to methods for treating restenosis using antisense osteopontin oligonucleotide sequences, and in particular, to treating restenosis following vascular surgery.

BACKGROUND OF THE INVENTION

Atherosclerosis (for review see Ross, R. (1993) Nature 362:801–809 and Hajjar et al., (1995) Amer. Scientist 83:460–467) is the principal cause of heart attacks, stroke, gangrene and loss of function of extremities. It accounts for approximately 50% of all mortalities in the USA, Europe and Japan (Ross, R. (1993) Nature 362:801–809). The present therapeutic strategies for severe atherosclerosis in coronary arteries rely on angioplasty procedures (e.g., percutaneous trans-luminal coronary angioplasty (PTCA), directional coronary atherectomy (DCA) or related angioplasty procedures), and coronary artery bypass surgery. For example, PTCA is the primary treatment modality in many patients with coronary heart disease. PTCA can relieve myocardial ischemia in patients with coronary artery disease by reducing lumen obstruction and improving coronary bloodflow.

While the use of interventional procedures has grown rapidly, reocclusion (or restenosis) of arteries is a serious complication which occurs in 30–50% of patients undergoing various angioplasty procedures within 3 days to 3 months. Restenosis results in significant morbidity and mortality and frequently necessitates further interventions, such as repeat angioplasty or coronary bypass surgery.

Although the processes responsible for restenosis are not completely understood, restenosis has been suggested to occur, at least in part, as a result of local inflammation, thrombosis and smooth muscle cell migration (Ferrell et al. (1992) Circulation 85:1630–1631) and proliferation (Austin et al. (1985) J. Am. Coll. Cardiol. 6:369–375; Giraldo et al. (1985) Arch. Pathol. Lab. Med. 109:173–175) within the intima of coronary arteries. To date, no post-angioplasty treatment has proven effective in the prevention or treatment of restenosis.

Thus, there is a need for methods and compositions for preventing and/or treating restenosis. Preferably, these methods and compositions are specific in their effect, easy to administer, and are effective over a short period of administration with minimal adverse side-effects.

SUMMARY OF THE INVENTION

The present invention discloses novel osteopontin antisense sequences which are useful for the treatment and prevention of restenosis. The present invention further discloses methods of diminishing osteopontin expression in a subject capable of developing restenosis in a tissue, methods of treating restenosis in a subject suspected of being capable of developing restenosis in a tissue, methods of reducing osteopontin expression in a subject undergoing angioplasty, methods of treating restenosis in a subject undergoing angioplasty, and methods of detecting restenosis in a subject.

In particular, the invention provides an antisense sequence comprising a nucleic acid sequence complementary to at least a portion of the human osteopontin cDNA polynucleotide listed herein as SEQ ID NO:15. While it is not intended that the present invention be limited to any particular antisense sequence, in one preferred embodiment the antisense sequence is selected from the group consisting of SEQ ID NO:9, SEQ ID NO:10, SEQ ID NO:11, SEQ ID NO:12, and SEQ ID NO:13. In addition, though the present invention is not limited to a particular type of linkage, in a more preferred embodiment, the antisense sequence comprises one or more phosphorothioate linkages. In a yet more preferred embodiment, the antisense sequence is entrapped in a liposome.

The present invention also provides pharmaceutical compositions comprising a pharmaceutically acceptable excipient and an antisense sequence comprising a nucleic acid sequence complementary to at least a portion of the polynucleotide of SEQ ID NO:15.

Further provided by the instant invention are methods of diminishing osteopontin expression, comprising: a) providing: i) a subject suspected of being capable of developing restenosis in a tissue; and ii) an osteopontin antisense sequence complementary of at least a portion of the polynucleotide of SEQ ID NO:15; and b) administering an amount of the sequence to the subject under conditions such that the osteopontin expression is diminished.

Without intending to limit the present invention to any particular subject, in one embodiment, the subject is undergoing angioplasty. Also without limiting the invention to a particular surgical method, in a more preferred embodiment, the angioplasty is selected from the group consisting of percutaneous trans-luminal coronary angioplasty and directional coronary atherectomy.

In an alternative embodiment, and without limiting the invention to a particular type of tissue, the tissue is coronary vascular tissue. In a preferred embodiment, the coronary vascular tissue is arterial.

In yet another alternative embodiment, without intending to limit the invention to a particular sequence, the osteopontin antisense sequence is selected from the group consisting of SEQ ID NO:9, SEQ ID NO:10, SEQ ID NO:11, SEQ ID NO:12 and SEQ ID NO:13.

Although it is not intended that the present invention be limited to a particular method of administering, in a further alternative embodiment, the administering is parenteral. In a preferred embodiment, the parenteral administering is intraarterial (i.e., to the artery which is subjected to angioplasty). In yet a more preferred embodiment, the intraarterial administering is by using a catheter. In a particularly preferred embodiment, the catheter is a double balloon catheter.

In yet another alternative embodiment, the osteopontin antisense sequence is entrapped in a liposome.

The instant invention further provides methods of treating restenosis, comprising: a) providing: i) a subject suspected of being capable of developing restenosis in a tissue; and ii) an osteopontin antisense sequence complementary to at least a portion of the polynucleotide of SEQ ID NO:15; and b) administering an amount of the sequence to the subject under conditions such that the restenosis is diminished.

The present invention further provides methods of reducing osteopontin expression in a subject undergoing angioplasty, comprising: a) providing: i) a subject undergoing angioplasty; and ii) an osteopontin antisense sequence complementary to at least a portion of the polynucleotide of SEQ ID NO:15; and b) administering an amount of the sequence to the subject under conditions such that osteopontin expression is diminished. In one embodiment, and without intending to limit the invention to a particular sequence, the osteopontin antisense sequence is selected from the group consisting of SEQ ID NO:9, SEQ ID NO:10, SEQ ID NO:11, SEQ ID NO:12 and SEQ ID NO:13. In a preferred embodiment, the osteopontin antisense sequence comprises one or more phosphorothioate linkages. In a more preferred embodiment, the osteopontin antisense sequence is entrapped in a liposome. In yet a more preferred embodiment, the administering is substantially contemporaneous with the angioplasty. In a particularly preferred embodiment, the administering is by using a catheter. In a most preferred embodiment, the catheter is a double balloon catheter.

The present invention also provides methods of treating restenosis in a subject undergoing angioplasty, comprising: a) providing: i) a subject undergoing angioplasty; and ii) an osteopontin antisense sequence complementary of at least a portion of the polynucleotide of SEQ ID NO:15; and b) administering an amount of the sequence to the subject under conditions such that restenosis is diminished.

Also provided by the present invention are methods of detecting restenosis in a first subject, comprising detecting a higher level of osteopontin in a first tissue of a first subject suspected of being capable of developing restenosis in a second tissue relative to a level of osteopontin in said first tissue of a second subject substantially free of restenosis in said second tissue. In one embodiment, the first tissue is selected from the group consisting of blood and plasma. In a preferred embodiment, the first tissue comprises monocytes comprising the osteopontin. In a more preferred embodiment, the second tissue is coronary vascular tissue. In yet a more preferred embodiment, the coronary vascular tissue is arterial.

BRIEF DESCRIPTION OF THE DRAWINGS

FIG. 1, panel A, shows expression by RT-PCR (upper two panels), and Western analysis (lower panel) in log-phase and confluent CASMCs. FIG. 1, panel B, shows expression of OPN protein in semiconfluent CASMCs by immunoprecipitation followed by Western blotting. FIG. 1, panel C, shows an autoradiogram of affinity cross-linked OPN in sub-receptor complex in subconfluent cultured CASMCs. FIG. 1, panel D, shows the results of an OPN binding study.

FIG. 2 shows the effect of OPN on CASMC (A) migration, (B) ECM-invasion, and (C) proliferation.

FIG. 3 shows (A) the detection of OPN-mRNA by in situ hybridization in coronary atherectomy arterial tissue (panels a and b), and in normal coronary arteries (panels c and d); (B) the detection of OPN-mRNA by RT-PCR in normal coronary arteries (panel a), and in coronary atherectomy arterial tissue (panel b); (C) the detection of OPN protein by Western blot analysis in control (panel a) and coronary atherectomy tissues (panel b).

FIG. 5 shows the nucleotide sequence (SEQ ID NO:15) of a cDNA of human osteopontin. This sequence contains a 5' untranslated region of 67 bases, followed by 942 bases encoding 314 amino acids, and 415 bases of the 3' untranslated region.

FIG. 8 shows the nucleotide sequence (SEQ ID NO:16) and deduced amino acid sequence (SEQ ID NO:17) of rat osteopontin.

DEFINITIONS

Figure 1A:
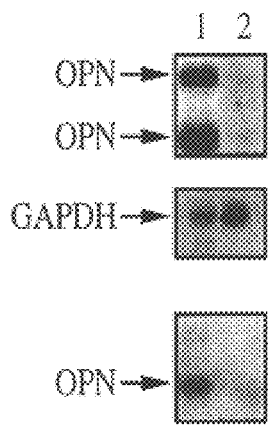
FIG. 1 shows the characterization of OPN expression in cultured CASMCs.
Figure 1B:
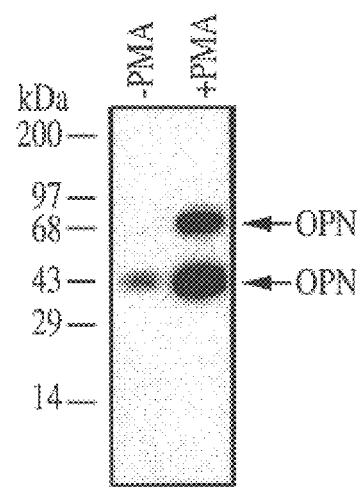
Figure 1C:
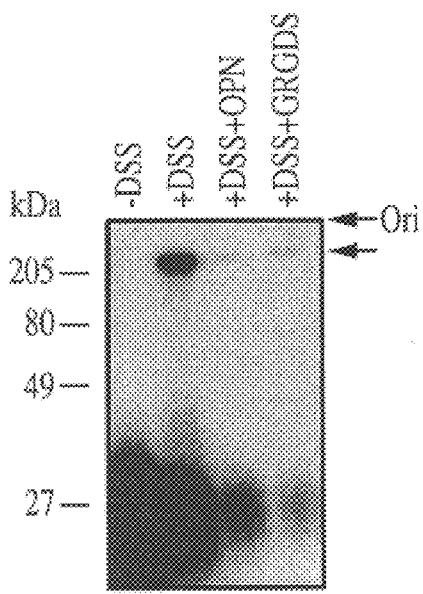
Figure 1D:
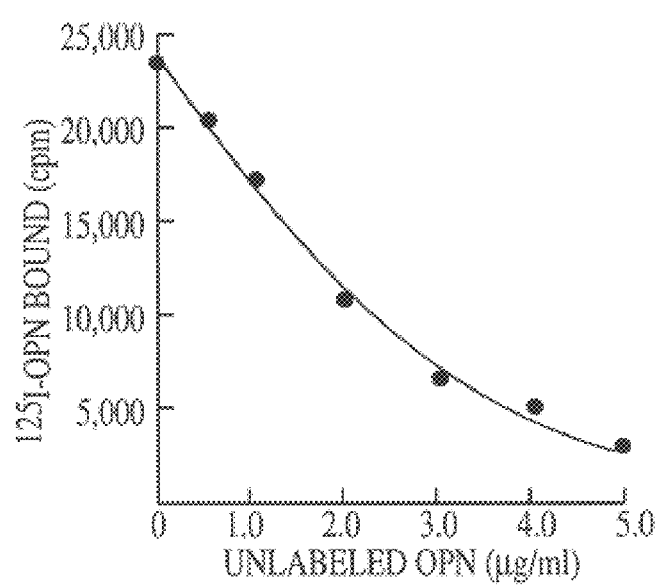

The term "restenosis" refers to a recurrence of stenosis. The term "stenosis" as used herein refers to a narrowing of any canal in the circulatory system including, but not limited to, valves (e.g., aortic stenosis which involves narrowing of the aortic valve orifice), coronary arteries (e.g., coronary ostial sclerosis which involves narrowing of the mouths of the coronary arteries), carotid arteries, renal arteries, etc. Restenosis generally results from neointimal hyperplasia. The term "neointimal hyperplasia" refers to the development of a proliferative lesion in the intimal layer of a blood vessel. Neointimal hyperplasia results, for example, from migration of smooth muscle cells of the tunica media layer of the blood vessel toward the lumen into the subintimal space below the endothelium (i.e., the inner lining of the blood vessel). These smooth muscle cells proliferate within the intimal space and create a "mass effect" that narrows the vessel lumen and reduces oxygenation and nutritive blood flow.

The term "mRNA" as used herein refers to mature, processed mRNA or to unprocessed, nuclear pre-mRNA transcribed from a gene sequence.

The term "liposome" as used herein refers to a lipid-containing vesicle having a lipid bilayer as well as other lipid carrier particles which can entrap antisense oligonucleotides. Liposomes may be made of one or more phospholipids, optionally including other materials such as sterols. Suitable phospholipids include phosphatidyl cholines, phosphatidyl serines, and many others that are well known in the art. Liposomes can be unilamellar, multilamellar or have an undefined lamellar structure.

The terms "entrap" and "incorporate" when made in reference to an oligonucleotide in a liposome are used herein to mean that the oligoncucleotide is at least partially contained somewhere within the wall of the liposome. Thus, an oligonucleotide entrapped in a liposome refers to the presence of the oligonucleotide either partially or completely within the lipid vesicle or within a wall of the lipid vesicle. The molar ratio of lipids in the liposome to the oligonucleotide entrapped in the liposome is preferably between about 100:1 and about 10,000:1, more preferably between about 500:1 and about 5,000:1, and most preferably about 1,000:1.

As used herein, the term "therapeutic amount" refers to that amount of a compound required to reduce, delay, or eliminate undesirable pathologic effects in a subject. A "therapeutic amount" of a compound when made in reference to restenosis refers to that amount of the compound which would diminish restenosis.

The term to "diminish restenosis" as used herein in reference to the effect of a particular composition or of a particular method is meant to reduce, delay, or eliminate restenosis as compared to the level of restenosis observed in the absence of treatment with the particular composition or method. As used herein, the term "reducing" restenosis refers to decreasing the intimal thickening that results from stimulation of smooth muscle cell proliferation. The term "delaying" restenosis refers to increasing the time period between removal of a stenosis (e.g., by use of surgical procedures) and onset of visible intimal hyperplasia (e.g., observed histologically or by angiographic examination). The term "eliminating" restenosis refers to completely "reducing" intimal thickening and/or completely "delaying" intimal hyperplasia in a subject to an extent which makes it no longer necessary to surgically intervene in order to re-establish a suitable blood flow through the vessel by surgical means (e.g., by repeating angioplasty, atherectomy, or coronary artery bypass surgery). The effects of diminishing restenosis in a human subject may be determined by methods routine to those skilled in the art including, but not limited to, angiography, ultrasonic evaluation, fluoroscopic imaging, fiber optic endoscopic examination or biopsy and histology. The effects of diminishing restenosis in a non-human animal subject may be determined by, for example, methods described herein including a reduction in the intimal/media cross-sectional ratio as measured by light microscopy of formalin-fixed tissue.

The term "substantially free of restenosis" when used in reference to a tissue of a subject refers to a subject in which clinical symptoms of restenosis in the tissue are substantially absent. Methods for determining substantial absence of clinical symptoms are known in the art. For example, the substantial absence of restenosis in coronary arterial vessels may be determined, for example, by cardiac catheterization and coronary angiograms which are capable of revealing the absence or presence of restenotic lesions, as well as by a thallium stress test which is capable of determining coronary blood flow that is indicative of occlusion by restenotic lesions.

The term to "diminish osteopontin expression" as used herein in reference to the effect of a particular composition or of a particular method on a tissue is meant to reduce the level of osteopontin expression in that tissue to a quantity which is less than the quantity of osteopontin expression in a corresponding control tissue which is, for example, not treated with that composition or method. For example, in order to determine whether a composition diminishes osteopontin expression in arterial atherectomy tissue from a subject, an arterial atherectomy tissue sample is removed from the subject, treated in the presence or absence of the composition, and the level of osteopontin expression measured in the arterial atherectomy tissue which had been treated in the presence or absence of the composition. The detection of a level of osteopontin expression in the arterial atherectomy tissue which had been treated with the composition that is lower than the level of osteopontin expression in the arterial atherectomy tissue which had not been treated with the composition demonstrates that the composition diminishes osteopontin expression.

The term "higher levels of plasma osteopontin" when made in reference to a first subject suspected of being capable of developing restenosis in a tissue refers to a quantity of plasma osteopontin in the first subject which is greater than the quantity of plasma osteopontin in a second subject substantially free of restenosis in that tissue, preferably at least twice as great as, more preferably at least five times as great as, and most preferably at least ten times as great as the quantity in the second subject as determined by, for example, Western blot analysis of osteopontin and immunofluorescence for detection of osteopontin as described herein.

The term "antisense" as used herein refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Sense mRNA generally is ultimately translated into a polypeptide. Thus an "antisense" sequence is a sequence having the same sequence as the non-coding strand in a DNA duplex. The term "antisense mRNA" refers to a ribonucleotide sequence whose sequence is complementary to an "antisense" sequence.

The term "oligonucleotide analog" as used herein refers to an oligonucleotide which comprises non-naturally-occurring portions. Thus, an oligonucleotide analog may have one or more altered sugar moieties, inter-sugar linkages, or altered base units. Altered inter-sugar linkages include, for example, substitution of the phosphodiester bonds of the oligonucleotide with sulfur-containing bonds, phosphorothioate bonds, alkyl phosphorothioate bonds, N-alkyl phosphoramidates, phosphorodithioates, alkyl phosphonates and short chain alkyl or cycloalkyl structures.

The term "portion" when used in reference to a nucleotide sequence refers to fragments of that nucleotide sequence. The fragments may range in size from 5 nucleotide residues to the entire nucleotide sequence minus one nucleic acid residue.

As used herein, the terms "vector" and "vehicle" are used interchangeably in reference to nucleic acid molecules that transfer DNA segment(s) from one cell to another.

The term "expression vector" or "expression cassette" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "recombinant protein" or "recombinant polypeptide" as used herein refers to a protein molecule which is expressed using a recombinant DNA molecule.

As used herein, the terms "complementary" or "complementarity" when used in reference to polynucleotides refer to polynucleotides which are related by the base-pairing rules. For example, or the sequence 5'-AGT-3' is complementary to the sequence 5'-ACT-3'. Complementarity may be "partial," in which one or more nucleic acid bases in one strand is not matched according to the base pairing rules with a nucleic acid base in another strand. Or, there may be "complete" or "total" complementarity between the nucleic acids. The degree of complementarity between nucleic acid strands has significant effects on the efficiency and strength of hybridization between nucleic acid strands. This is of particular importance in methods which depend upon binding between nucleic acids.

The term "homology" when used in relation to nucleic acids refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

The term "hybridization" as used herein includes "any process by which a strand of nucleic acid joins with a complementary strand through base pairing." [Coombs J (1994) *Dictionary of Biotechnology*, Stockton Press, New York N.Y.].

The terms "hybridizable" and "capable of hybridizing" refer to the ability of one strand of nucleic acid to join with a completely or partially complementary strand via base pairing under high or low stringency conditions.

As used herein the term "stringency" is used in reference to the conditions of temperature, ionic strength, and the presence of other compounds such as organic solvents, under which nucleic acid hybridizations are conducted. "Stringency" typically occurs in a range from about $T_m$ to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" SEQ ID NO:15 or fragments thereof will hybridize to its exact complement and closely related sequences.

The term "atherosclerosis" refers to a form of arteriosclerosis in which deposits of yellowish plaques (i.e., atheromas) containing cholesterol, lipid material, and lipophages are formed within the intima and inner media of large and medium-sized arteries.

The term "angioplasty" refers to surgery of blood vessels as exemplified by percutaneous transluminal coronary angioplasty (PTCA), wherein a balloon in a catheter is inflated to open the lumen of an artery blocked by atherosclerotic plaques to allow blood flow, and by directional coronary atherectomy (DCA), wherein an atherosclerotic plaque is removed from the lumen of a blocked artery.

DESCRIPTION OF THE INVENTION

The present invention provides sequences capable of inhibiting osteopontin (OPN) expression. More particularly, the sequences provided herein are antisense OPN sequences. Also provided by the invention are methods for treating restenosis. The compositions and methods provided by this invention are useful in treating restenosis associated with traumatic injury to vascular walls. In particular, the compositions and methods provided herein are useful for treating restenosis following vascular surgery, e.g., percutaneous transluminal coronary angioplasty (PCTA), directional coronary atherectomy (DCA), and the like. Moreover, the compositions described herein find utility in inhibiting osteopontin expression in vitro and in in vivo animal model systems.

To facilitate understanding of the inventions provided herein, the description of the invention is divided into (a) antisense osteopontin, and (b) methods for treating restenosis.

A. Antisense Osteopontin Sequences

Osteopontin was first identified in 1979 (Senger et al. (1979) Cell 16:885–893) as a transformation-related phosphoprotein and was later named osteopontin (OPN) (Franzen et al. (1985) Biochem. J. 232:715–724). It is a secreted non-collagenous, glycosylated phosphoprotein (Oldberg et al. (1988) J. Biol. Chem. 263:19433–19436; Nemir et al. (1989) J. Biol. Chem. 264:18202–18208; Craig et al. (1989) Int. J. Cancer 46:133–137; Denhardt et al. (1993) FASEB J. 7:1475–1482) which binds to cell surface integrins (Hynes (1992) Cell 69:11–25), a family of heterodimeric glycoprotein subunits designated α and β. These integrins act as cell surface receptors for many ligands, including OPN (Oldberg et al. (1986) Proc. Natl. Acad. Sci.

USA. 83:8819–8823). OPN gene expression has been reported to be a distinctive feature of rat aortic smooth muscle cells (Giachelli et al. (1991) Biochem. Biophys. Res. Commun. 177:867–873). Moreover, rat and bovine smooth muscle cell (SMC)-migration is promoted by OPN (Liaw et al. (1994) Circ. Res. 74:214–224). It has also been demonstrated that high levels of OPN-mRNA and protein are detectable in the rat and human aorta, and carotid arteries during neointima formation (Ikeda et al. (1993) J. Clin. Invest. 92:2814–2820; Giachelli et al. (1993) J. Clin. Invest. 92:1686–1696; Shanahan et al. (1994) J. Clin. Invest. 93:2393–2402; Liaw et al. (1995) J. Clin. Invest. 95:713–724). OPN overexpression has been shown to associate with rat arterial SMC proliferation (Gadeau et al. (1993) Arteriosclerosis & Thrombosis 13:120–125), and its levels have been reported to increase in atherosclerotic plaques and during restenosis which follows balloon angioplasty (see, Rodan (1994) "Osteopontin overview," In "Annals New York Acad. Sci." pp 1–5). Most interestingly, it has been demonstrated that subjecting cultured cells to intermittent compressive force, similar to the forces which may be produced by some angioplasty procedures, causes OPN overexpression (Kubota et al (1993) Archs. Oral Biol. 38:23–30).

Without intending to limit the invention to a particular theory, data presented herein suggest that one mechanism which contributes to restenosis is the migration of coronary artery smooth muscle cells (CASMCs) to the site of injury caused by angioplasty and subsequent proliferation of migrated CASMCs.

Also without limiting the invention to any particular theory or mechanism, data from in vitro and in vivo investigations presented herein suggest that there may be a cascade of events which lead to the development of restenosis after angioplasty and that OPN plays both autocrine and paracrine receptor-mediated roles which critically affect the biology of coronary artery smooth muscle cells (CASMCs). OPN has been reported to have chemotactic properties (Liaw et al. (1994) Circ. Res. 74:214–224) and has been demonstrated to induce proliferation in rat aortic smooth muscle cells (SMCs) (Gadeau et al. (1993) Arteriosclerosis & Thrombosis 13:120–125). Thus, a likely scenario is that the inflammatory stimulus generated by the trauma of angioplasty is the triggering event which causes infiltration of monocytes and macrophages into the vascular smooth muscle layer. Since activated monocytes and macrophages are known to secrete OPN, the secreted OPN may bind to $\alpha_v\beta_3$ integrin on CASMCs, which may in turn respond by expressing yet more OPN. Secreted OPN then interacts with CASMCs in an autocrine or paracrine fashion and promotes their migration towards the intima where the angioplasty-induced injury has occurred. These cells then invade the ECM and finally, proliferate to cause reocclusion.

It has been reported that vascular smooth muscle cells, when stimulated with vitronectin, undergo haptotaxis (Naito et al. (1991) Exp. Cell Res. 194:154–156), a process in which the cells migrate towards an increasing gradient of a chemoattractant. More recently, Senger et al. (Senger et al. (1996) Am. J. Pathol. 149:293–305) have demonstrated that OPN and its GRGDS-containing thrombin cleavage fragment promote tumor and vascular endothelial cell haptotaxis respectively, via the $\alpha_v\beta_3$ integrin. Data presented herein demonstrate that plasma OPN levels dramatically increase following treatment of patients with the DCA procedure. This increase may create an increasing gradient of this protein from the media of the arterial wall (where the CASMCs are normally located) to the lumen of the artery, where the highest concentration of OPN may be found. This data, combined with further results provided herein, which demonstrate the ability of CASMCs to migrate towards a higher concentration of OPN, to invade ECM, and to proliferate in response to OPN may explain the role of OPN in arterial occlusion (i.e., restenosis) following DCA procedure. Without intending to limit the invention to any theory, it is hypothesized that the establishment of such an OPN gradient in vivo results in the migration of CASMCs from their original location in the arterial media, invasion of the arterial ECM, and arrival at their destination in the intima. It is further hypothesized that CASMCs arriving at the intima proliferate in response to OPN-stimulation, thus resulting in reocclusion.

While there may be other factors involved in the pathogenesis of this disease process, results presented herein demonstrates that OPN and its $\alpha_v\beta_3$ integrin receptor play an essential role not only in stimulating the migration and ECM-invasion but also of proliferation of CASMCs.

Importantly, data presented herein which demonstrate for the first time that lipofection of CASMCs with OPN-antisense phosphorothioate-oligonucleotides results in a drastic inhibition of CASMC proliferation has far reaching clinical significance, i.e., that reocclusion of vessels following vascular trauma may be diminished by administration of OPN-antisense oligonucleotide sequences.

The present invention provides antisense OPN sequences. In one embodiment, the antisense OPN sequence of the invention is SEQ ID NO:9. In another embodiment, the antisense OPN sequence provided herein is SEQ ID NO:10. In yet another embodiment, the antisense OPN sequence disclosed by the present invention is SEQ ID NO:11. In a further embodiment, the antisense OPN sequence is SEQ ID NO:12. In yet a further embodiment, the antisense OPN sequence of the invention in SEQ ID NO:13.

The antisense OPN sequences of the invention are not limited to the antisense OPN sequences provided herein. Any antisense sequence is contemplated to be within the scope of this invention if it is capable of reducing the level of expression of OPN to a quantity which is less than the quantity of OPN expression in a corresponding control tissue which is (a) not treated with the antisense OPN sequence, (b) treated with a corresponding sense OPN sequence, or (c) treated with a nonsense sequence. The terms "reducing the level of expression of OPN," "diminishing osteopontin expression" and grammatical equivalents thereof refer to reducing the level of OPN expression to a quantity which is preferably 30% less than the quantity in a corresponding control tissue, more preferably 90% less than the quantity in a corresponding control tissue, and most preferably is at the background level of, or is undetectable by, a Western blot analysis of OPN, immunofluorescence for detection of OPN, reverse transcription polymerase chain (RT-PCR) reaction for detection of OPN mRNA, or by in situ hybridization for detection of OPN mRNA as described herein. When a background level or undetectable level of OPN or of OPN mRNA is measured, this may indicate that OPN is not expressed, and thus that OPN is ineffective. A reduced level of OPN need not, although it may, mean an absolute absence of expression of OPN. The invention does not require, and is not limited to, antisense OPN sequences which eliminate expression of OPN.

Antisense osteopontin sequences capable of reducing the level of osteopontin expression include, for example, sequences which are capable of hybridizing with at least a portion of SEQ ID NO:15 under high stringency or low stringency conditions as described herein.

1. Design

Antisense OPN sequences within the scope of this invention may be designed using approaches known in the art. In a preferred embodiment, the antisense OPN sequences are designed to be hybridizable to OPN mRNA encoded by the coding region of the OPN gene as shown in FIG. 5, (SEQ ID NO:15) (Kiefer et al. (1989) Nucleic Acids Res. 17:3306). Antisense OPN sequences which are designed to hybridize to OPN mRNA which is encoded by the OPN gene coding region interfere with the normal function of the mRNA, e.g., translocation to the situs for protein translation, binding to ribosomes, etc., thus resulting in reduced translation of OPN mRNA.

Alternatively, antisense OPN sequences may be designed to reduce transcription by hybridizing to upstream nontranslated sequences, thereby preventing promoter binding to transcription factors.

In a preferred embodiment, the antisense oligonucleotide sequences of the invention range in size from about 8 to about 100 nucleotide residues. In yet a more preferred embodiment, the oligonucleotide sequences range in size from about 8 to about 30 nucleotide residues. In a most preferred embodiment, the antisense OPN sequences have 20 nucleotide residues.

However, the invention is not intended to be limited to the number of nucleotide residues in the oligonucleotide sequence disclosed herein. Any oligonucleotide sequence which is capable of reducing expression of OPN is contemplated to be within the scope of this invention. For example, oligonucleotide sequences may range in size from about 3 nucleotide residues to the entire OPN cDNA sequence of FIG. 5. The art skilled know that the degree of sequence uniqueness decreases with decreasing length, thereby reducing the specificity of the oligonucleotide for the OPN mRNA.

In a preferred embodiment, the antisense oligonucleotide sequences of the invention comprise an oligonucleotide analog. In yet a more preferred embodiment, the oligonucleotide analog contains one or more phosphorothioate bonds.

However, the antisense oligonucleotides of the invention are not limited to oligonucleotide analogs with phosphorothioate linkages. The invention is contemplated to include within its scope any oligonucleotide sequences so long as it is capable of hybridizing under low stringency or high stringency conditions to the target human OPN mRNA. Oligonucleotides which hybridize under high stringency conditions to the target human OPN mRNA are preferred since such oligonucleotides exhibit high specificity for the human OPN mRNA. Oligonucleotides which are contemplated to be within the scope of this invention include, for example, the antisense oligonucleotide sequences of the invention may comprise naturally occurring nucleotide residues as well as nucleotide analogs. Nucleotide analogs may include, for example, nucleotide residues which contain altered sugar moieties, altered inter-sugar linkages (e.g., substitution of the phosphodiester bonds of the oligonucleotide with sulfur-containing bonds, phosphorothioate bonds, alkyl phosphorothioate bonds, N-alkyl phosphoramidates, phosphorodithioates, alkyl phosphonates and short chain alkyl or cycloalkyl structures), or altered base units. Oligonucleotide analogs are desirable, for example, to increase the stability of the antisense oligonucleotide compositions under biologic conditions since natural phosphodiester bonds are not resistant to nuclease hydrolysis. Oligonucleotide analogs may also be desirable to improve incorporation efficiency of the oligonucleotides into liposomes, to enhance the ability of the compositions to penetrate into the cells where the nucleic acid sequence whose activity is to be modulated is located, in order to reduce the amount of antisense oligonucleotide needed for a therapeutic effect thereby also reducing the cost and possible side effects of treatment.

2. Synthesis

Antisense OPN oligonucleotide sequences may be synthesized using any of a number of methods known in the art, as well as using commercially available services (e.g., Genta, Inc.). Synthesis of antisense oligonucleotides may be performed, for example, using a solid support and commercially available DNA synthesizers. Alternatively, antisense oligonucleotides may also be synthesized using standard phosphoramidate chemistry techniques. For example, it is known in the art that for the generation of phosphodiester linkages, the oxidation is mediated via iodine, while for the synthesis of phosphorothioates, the oxidation is mediated with 3H-1,2-benzodithiole-3-one,1,-dioxide in acetonitrile for the step-wise thioation of the phosphite linkages. The thioation step is followed by a capping step, cleavage from the solid support, and purification on HPLC, e.g., on a PRP-1 column and gradient of acetonitrile in triethylammonium acetate, pH 7.0.

C. Methods for Treating Restenosis

The present invention provides methods for the treatment of restenosis. In one embodiment, the methods of the invention comprise administering a therapeutic amount of an OPN antisense oligonucleotide to a subject under conditions such that restenosis symptoms are diminished. In a preferred embodiment, the restenosis sought to be alleviated by the methods of the invention is that which may follow vascular trauma from vascular surgical procedures such as angioplasty. Angioplasty may be performed, for example, by percutaneous trans-luminal coronary angioplasty (PTCA) or by directional coronary atherectomy (DCA). PTCA generally involves inserting a catheter (i.e., a plastic tube) with a balloon on the end into the blood vessel and inflating the balloon to high pressures to dilate the lumen of a blood vessel that is narrowed e.g. by atherosclerosis (i.e., hardening of the artery). DCA involves inserting a catheter with a probe at the end (the probe is generally metallic in order to permit X-ray visualization during the surgical procedure) into the blood vessel and removing atherosclerotic tissue from the lumen of the vessel with the probe.

However, the methods of the invention are not limited to vascular trauma from angioplastic procedures. Any procedure which results in restenosis is contemplated to be within the scope of the invention. Such procedures include, for example, atheroectomy, placement of a stent (e.g., in a vessel), thrombectomy, and grafting. Atheroectomy may be performed, for example, by surgical excision, ultrasound or laser treatment, or by high pressure fluid flow. Introduction of a stent generally involves introducing a wire-mesh cylinder within the lumen of a stenotic vessel to increase the lumen diameter and restore blood flow. Thrombectomy may be performed by, for example, introducing into the vessel a pneumatically operated catheter which is fitted with rotating blades at the tip to remove the thrombus or clot. Grafting may be achieved, for example, by vascular grafting using natural or synthetic materials, or by surgical anastomosis of vessels such as during organ grafting.

1. Delivery

In a preferred embodiment, the antisense sequences provided herein are delivered as liposomal oligonucleotides. In a more preferred embodiment, the liposomal composition used to entrap the antisense oligonucleotide sequences of the invention is "LIPOFECTIN." "LIPOFECTIN" is a 1:1 (w/w) formulation of the cationic lipid N-[1-(2,3- dioleyloxy)propyl]-N,N,N-trimethylammonium chloride (DOTMA) and dioleoyl phosphatidylethanolamine (DOPE). The positively charged and neutral lipids from liposomes that can complex with nucleic acids. Successful direct physical transfer of genes into intact blood vessels in vivo using cationic liposomes (e.g., "LIPOFECTIN") has been reported [Nabel et al. (1990) Science 244:1285–1288]. Nabel et al. reported that after initial incubation with the liposomes using a double-balloon catheter, expression of the transfected DNA could be detected in the vessel wall for up to five months. Lim et al. [Lim et al. (1991) Circulation 83:2007–2011] have also reported successful cationic-lipid-mediated gene transfer into intact canine coronary and peripheral arteries. Successful lipofection of circulatory vessels has also been reported by Lynch et al. [Lynch et al. (1992) Proc. Natl. Acad. Sci. USA 89:1138–1142] and Flugelman et al. [Flugelman et al. (1992) Circulation 85:1110–1117].

The invention is not limited to the type or composition of the liposome. Any liposome which may be deemed useful by one of skill in the art for use with the antisense molecules of the invention is contemplated to be within the scope of this invention. Liposomes of different compositions are known in the art and are exemplified by those described herein or those known in the art [e.g., U.S. Pat. No. 5,417,978 the contents of which are herein incorporated by reference].

Delivery of the antisense oligonucleotides of the invention is not limited to the use of liposomal oligonucleotides. The antisense oligonucleotides provided herein may be delivered to a target cell in various forms including, but not limited to, as free oligonucleotides or as oligonucleotides complexed with other compositions.

Where the antisense oligonucleotides of the invention are complexed with other compositions, such as with a combination of liposomes and the protein coat of the inactivated hemagglutinating virus of Japan (HVJ) [Morishita et al. (1993) Proc. Natl. Acad. Sci. USA 90:8474–8478], or with a combination of liposomes, inactivated HVJ coat protein and nuclear protein [Kaneda et al. (1989) Science 243:375–378; von der Leyen et al. (1994) FASEB J. 8:A802]. Antisense oligonucleotides complexed with liposomes and the protein coat of HVJ have been shown to result in a more rapid cellular uptake and a 10-fold higher transfection efficiency of antisense oligonucleotides or plasmid DNA than lipofection or passive uptake methods [Morishita et al. (1993) J. Clin. Invest. 91:2580–2585]. In an alternative embodiment, antisense oligonucleotide sequences may be administered in pluronic gels (BASF Wyandotte Corp., Wyandottee, Mich.).

Transfer of antisense sequences into vascular smooth muscle cells may be accomplished by other methods known in the art, including re-implantation of cells modified in vitro [for a review, see, Dzau et al. (1993) Trends Biotechnol. 11:205–210].

Alternatively, antisense sequences may be introduced into a cell by transferring into the target cell a vector capable of expression of the antisense sequence. In particular, viral-vector mediated gene transfer is known in the art such as such as retrovirus, adenovirus, Hemagglutinating virus of Japan (HVJ; also referred to as Sendai virus). Vectors which express antisense OPN oligonucleotide sequences can flood cells with untranslatable antisense mRNA sequences which inhibit expression of OPN either by inhibiting transcription of the OPN gene or inhibiting translation of an OPN-encoding mRNA. For example, vectors derived from oncoretroviruses, such as the Moloney leukemia virus (MLV), integrate the transgene in the genome of the target cells without transferring any viral gene, two properties considered crucial for the sustained expression of the transgene. These retroviral vectors may be particularly suitable for targeting OPN gene expression in proliferating human smooth muscle cells since these vectors only transduce cells that divide shortly after infection [Miller et al. (1990) Mol. Cell. Biol. 10:4239–4242], and do not transduce non-dividing cells [Naldini et al. (1996) Science 272:263–267].

Other virus-derived vectors which are suitable for in vivo gene transfer are available in the art including human immunodeficiency virus-derived vectors [Naldini et al. (1996) Science 272:263–267; Naldini et al. (1996) Proc. Natl. Acad. Sci. USA 93:11382–11388], adenovirus-derived vectors [Lemarchand et al. (1993) Circ. Res. 72:1132–1138], retroviruses such as BAG and BAL [Wilson et al. (1989) Science 244:1344–1346]. While adenovirus-derived vectors are available, and their expression is temporary (i.e., making them suitable for treatment of acute disease such as restenosis following angioplastic surgery) these vectors are not preferred since an immune response is raised in vivo against the transduced cells thus resulting in inflammation which would exacerbate the risk of restenosis. Similarly, while vectors derived from retroviruses (e.g., human immunodeficiency virus) are available, their use is not preferred as these vectors are expressed only in non-dividing cells, and would therefore be expected not to transduce proliferating smooth muscle cells during restenosis.

Methods for the design of a viral vector are known in the art. Generally, the design of a viral vector system relies upon the segregation in the viral genome of cis-acting sequences involved in its transfer to target cells from trans-acting sequences encoding the viral proteins. The prototype vector particle is assembled by viral proteins which are expressed from constructs stripped of all cis-acting sequences. These sequences are instead used to frame the expression cassette for the transgene driven by an heterologous promoter. As the particle will transfer only the latter construct, the infection process is limited to a single round without spreading. The safety and efficiency of an actual vector system depends on the extent to which complete segregation of cis- and trans-acting functions is obtained.

2. Dosage

Those skilled in the art will recognize that the appropriate therapeutic dosage of the oligonucleotides of the invention for a given vascular surgical procedure may be determined in in vitro and in vivo animal model systems, and in human preclinical trials. in vitro testing may be accomplished using commercially available human coronary artery smooth muscle cells (CASMCs) coupled with determination of the effect of antisense oligonucleotide treatment on OPN expression as measured by Western blot analysis, cellular proliferation and migration, and on extracellular matrix invasion, as described herein. In vivo testing of a suitable therapeutic dose may be accomplished using art-accepted animal models such as the rat carotid artery model described herein, in which the effect of antisense oligonucleotide treatment on OPN expression, DNA synthesis and intimal/medial cross-sectional ratios are determined.

Generally, where the antisense oligonucleotides of the invention are delivered as liposomal oligonucleotides, the dose of the antisense oligonucleotide ranges preferably between about 1 $\mu$M and about 500 $\mu$M, more preferably between about 1 $\mu$M and about 100 $\mu$M, and most preferably between about 5 $\mu$M and about 15 $\mu$M. 3. Delivery Routes In a preferred embodiment, the antisense oligonucleotides of the present invention are administered locally to the site of vascular trauma by using an infusion catheter. Infusion catheters are commercially available (e.g., C. R. Bard Inc., Billerica, Mass.) and known in the art (e.g., infusion catheters described by Wolinsky in U.S. Pat. No. 4,824,436, or by Spears in U.S. Pat. No. 4,512,762, the contents of both patents are herein incorporated by reference). The infusion catheter may be conveniently a double balloon or quadruple balloon catheter with a permeable membrane.

The invention is not limited to local delivery by catheter. The antisense oligonucleotides of the invention may be delivered to the smooth muscle layers of a mammalian artery wall by a number of routes such as, for example, the biodegradable materials exemplified by those described in U.S. Pat. No. 4,929,602 (the contents of which are incorporated by reference) which are impregnated with the sequences of the invention.

Alternatively, local delivery of the antisense nucleotides of the invention may be achieved by using, for example, implanted osmotic pumps, or by inclusion of the oligonucleotide sequences into pluronic gels such as those available from BASF Wyandotte Corp., Wyandotte, Mich. One of skill in the art would appreciate that the antisense sequences of the present invention may need only to be delivered in a therapeutic dosage sufficient to expose the proximal (i.e., 6 to 9) cell layers of the intimal or tunica media cells which line the lumen of a blood vessel. Such a dosage can be determined empirically by, for example, infusing vessels from suitable animal model systems and using immunohistochemical methods to detect the presence and cellular localization of OPN protein. Alternatively, dosage may also be empirically determined by conducting suitable in vitro investigation as described herein.

It is further preferred, though not required, that the use of an infusion catheter to administer the antisense sequences of the invention be performed substantially contemporaneously (i.e., during the same surgical procedure which is employed to alleviate stenosis) with the performance of the surgical procedures which result in vascular trauma. Such contemporaneity is desirable since it (a) is convenient, (b) avoids unnecessary further trauma to the blood vessels which otherwise would result from independent catheter infusion and angioplasty procedures, and (c) provides a greater probability of preventing restenosis since significant elevation of the levels of circulating OPN occur as early as 24 hours within performance of an angioplastic procedure as disclosed by this invention, and since approximately 30–50% of the patients undergoing angioplastic procedures suffer from restenosis within 3 days to 3 months.

One of skill in the art would recognize that a suitable therapeutic dosages of antisense oligonucleotides administered in vivo by a catheter is dependent on several factors including, but not limited to, a) the atmospheric pressure applied during infusion; b) the time over which the composition administered resides at the vascular site; c) the nature of the employed composition which contains the oligonucleotides of the invention; and/or d) the nature of the vascular trauma and therapy desired. Those skilled in the art will recognize that infiltration of compositions containing antisense oligonucleotide sequences into the smooth muscle layers of a mammalian artery wall will probably be variable and will need to be determined on an individual basis. Such determination is routine, and follows similar principles as those known to and applied by practitioners in the art in using a multitude of drugs which are administered routinely.

While infusion catheters are contemplated to provide a preferred administration route, one of skill in the art would recognize that other methods for delivery or routes of administration may also be useful, e.g., injection by the intravenous, intralymphatic, intrathecal, intraarterial, or other intracavity routes. These routes are not preferred since attaining a therapeutic level at the site of potential restenosis would require administration of a large amount of oligonucleotide sequence which is costly One of skill in the art knows that the sequences of the invention may be administered using a number of pharmaceutically acceptable carriers (i.e., excipients). In a preferred embodiment, the pharmaceutically acceptable carrier is in liquid phase. Useful pharmaceutically acceptable carriers include generally employed carriers, such as phosphate buffered saline solution, water, emulsions (e.g., oil/water and water/oil emulsions) and wetting agents of various types.

4. Timing and Number of Doses

It is contemplated that administration of antisense sequences of the present invention may be continuous or intermittent, depending, for example, upon the recipient's physiological condition, whether the purpose of the administration is therapeutic or prophylactic and other factors known to those skilled in the art.

The methods of the invention are not limited to the number or timing of administration of the antisense oligonucleotide sequences provided herein. For example, dosages for the prevention of restenosis following angioplasty, may be applied prior to, simultaneously with, and/or subsequent to the surgical intervention procedure. In one embodiment of a dosing regimen, a "pre-loading" dose may be administered prior to or at the time of the intervention. A preloading dose may be a single pre-loading dose (i.e., where the oligonucleotides of the invention are administered at a single point in time) or a multiple pre-loading dose (i.e., where the oligonucleotides of the invention are administered at multiple points in time). For example, a single pre-loading dose may be administered about 24 hours prior to intervention, while multiple pre-loading doses may be administered daily for several days prior to intervention. In another embodiment of a dosing regimen, a "contemporaneous dose" may be administered, i.e. where the oligonucleotides of the invention are administered during the surgical intervention procedure. In yet another embodiment of a dosing regimen, a "follow up" dose may be delivered subsequent to the intervention surgical procedure. An example of a follow up dose is a daily administration one to two weeks or longer following intervention. One of skill in the art would appreciate that the dosing regimen is selected so as to minimize the proliferative effect of osteopontin following surgical intervention for a time sufficient to substantially reduce the risk of, or to prevent, restenosis. One of skill in the art also knows that the dosing regimens may be determined empirically by in vitro testing, in vivo testing in animal models, and by pre-clinical testing in human subjects. It is preferred, though not required, that a dosing regimen employ a contemporaneous dose.

The methods of the invention are not limited to the duration of administration of the antisense sequences provided herein. Administration may be for a short time (i.e., delivery over a period of time equal to or less than about 2–3 minutes) or chronic (i.e., continued or sporadic delivery which is continued over a period of time greater than 10 minutes). Administration for a short time may be useful to offset, at least partially, the strong stimulus for vascular smooth muscle cell proliferation caused by highly traumatic injuries or procedures such as angioplasty. On the other hand, chronic delivery of a lower dose delivered to the traumatized site may provide further protection against restenosis resulting from vascular smooth muscle cell proliferation in the traumatized area. In a preferred embodiment, administration is for a short time. More preferably, administration is for about 2–3 minutes.

EXPERIMENTAL

The following examples serve to illustrate certain preferred embodiments and aspects of the present invention and are not to be construed as limiting the scope thereof.

In the experimental disclosure which follows, the following abbreviations apply: CASMC (coronary artery smooth muscle cells); OPN (osteopontin); DCA (directional coronary atherectomy); DSS (disuccinimidyl suberate); PMSF (phenyl methyl sulfonyl-fluoride); PBS (phophate buffered saline); PMA (phosbol 12-myristate 13-acetate); RT-PCR (reverse transcription polymerase chain reaction); ECM (extracellular matrix); FCM (fibroblast conditioned medium); American Histolabs (Rockville, Md.); BASF Wyandotte Corporation (Wyandotte, Mich.); Boehringer Mannheim (Indianapolis, Ind.); Charles Rivers (Michigan, OH); Chemicon (Temecula, Calif.); (Collaborative Research, Bedford, Mass.); Clonetics (San Diego, Calif.); Costar (Cambridge, Mass.); ICN (Biomedicals, CA), Pharmacia Biotecnology, Inc. (Piscataway, N.J.); Sigma (St. Louis, Mo.).

Example 1

Expression of OPN mRNA and Protein in Cultured Human Coronary Artery Smooth Muscle Cells The pattern of OPN-mRNA and protein expression in proliferating cultured human coronary artery smooth muscle cells (CASMCs) was investigated using reverse transcription polymerase chain reaction (RT-PCR) and Western blot analysis on commercially available CASMCs. CASMCs (Clonetics) were cultured in smooth muscle cell basal medium (Clonetics) supplemented with insulin (5 µg/ml), human fibroblast growth factor (2 ng/ml), human epidermal growth factor (0.5 ng/ml) and 5% fetal calf serum in a humidified atmosphere of 5% $CO_2$ and 95% air at 37° C.

Prior to the determination of mRNA and protein expression, immunofluorescence was used in order to determine whether these cells are 100% smooth muscle cells using methods known in the art (Peri et al., (1994) DNA and Cell Biol. 13:495–503). Briefly, CASMCs during log phase of growth on microscopic slides were fixed in 4% buffered paraformaldehyde, embedded in paraffin and histological sections were prepared (American Histolabs). These cell samples were used for immunofluorescent detection of (a) OPN using a previously characterized rabbit OPN-antiserum (Chacklaparampil et al., (1996) Oncogene 12:1457–1467), (b) SMC-specific α-actin using a monoclonal antibody (clone 1A4) to human SMC-specific α-actin (Sigma), and (c) $\alpha_v\beta_3$ integrin using mouse monoclonal antibody to human $\alpha_v\beta_3$ (Chemicon). These cells expressed each of the three antigens (i.e., OPN, SMC-specific α-actin, and $\alpha_v\beta_3$ integrin) thus confirming their smooth muscle cell type.

A. Reverse Transcription Polymerase Chain Reaction

RNA from cultured CASMCs was extracted as previously described (Chomczynski et a. (1987) Anal. Biochem. 162:156159). Briefly, the CASMCs were grown in a 75 cm² flask, washed in ice-cold PBS three times and lysed in 2 ml of RNA Zol B (Tel-Test, TX). The cell lysates (1 ml each) were transferred to microcentrifuge tubes and 100 µl of chloroform were added to each tube. The upper aqueous layers were collected by centrifugation at 12,000 rpm for 15 min. in a clinical centrifuge and the contents (400 µl) transferred to another microcentrifuge tube. The RNA samples were precipitated by adding 400 µl of isopropanol, collected by centrifugation, washed with 75% cold ethanol and suspended in 15 µl DEPC-treated water. The concentration of RNA was measured by a spectophotometer.

The sequences of the primers and probe used for RT-PCR were derived from the sequence of human OPN cDNA shown in FIG. 5. The sequence of the antisense primer, hOPN-R (nt 928–909) was 5'-CTA CAA CCA GCA TAT CTT CA-3' (SEQ ID NO:1) and of the sense primer, hOPN-L (nt 418–437) was 5'-CAC CAG TCT GAT GAG TCT CA-3' (SEQ ID NO:2). The PCR products were detected by using a digoxigenin-labeled hOPN probe, i.e., hOPN-$P_1$ (nt 647–628)=5'-TCC ATG TGT GAG GTG ATG TC-3' (SEQ ID NO:3). Amplification of the cDNA of a control house-keeping gene, i.e., glyceraldehyde 3-phosphate dehydrogenase (GAPDH) was performed using the sense primer, GAPDH-L (nt 388–405) 5'-CCA TGG AGA AGG CTG GGG-3' (SEQ ID NO:4) and the anti-sense primer, GAPDH-R (nt 582–563) 5'-CAA AGT TGT CAT GGA TGA CC-3' (SEQ ID NO:5). The probe, GAPDH-P (nt 549–531) was 5'-CTA AGC AGT TGG TGG TGC A-3' (SEQ ID NO:6).

The results of RT-PCR are shown in FIG. 1A. Lane 1 contains CASMCs at log phase of growth; Lane 2 contains CASMCs from confluent cultures. The upper, middle and lower panels are OPN-mRNA, GAPDH mRNA, and OPN protein respectively. During log phase of growth these cells expressed elevated levels of OPN-mRNA (FIG. 1A, panel a: upper lane 1) compared to the confluent cultures (FIG. 1A, panel a: upper lane 2). The GAPDH-mRNA signals were identical (FIG. 1A, panel a: middle lanes 1 & 2) in both non-confluent and confluent cultures, demonstrating that these differences were not due to variability in gel loading or degradation of RNA during extraction.

The data in FIG. 1A panel a shows that OPN-mRNA and protein were easily detectable when the cells were in log phase of growth while the level was significantly lower when the cells reached confluence.

B. Western Blot Analysis

The level of OPN in CASMCs was detected by Western blot analysis as previously described (Chacklaparampil et al., (1996) Oncogene 12:1457–1467). Briefly, the specimens were homogenized in lysis buffer (50 mM Tris-HCl, pH 7.5 containing 150 mM NaCl, 1% Nonidet P40, 15 µg/ml leupeptin and 0.5 µM PMSF), and centrifuged at 12,000×g for 10 min. The supernatants were electrophoresed on a 4–20% gradient SDS-polyacrylamide gel and electrotransferred to nitrocellulose membrane. The membranes were blocked, incubated with rabbit anti-rat OPN antibody (previously characterized by Chaklaparampil et al. (Chacklaparampil et al., (1996) Oncogene 12, 1457–1467) (1:250 dilution) and detected with $^{125}$I-protein A (ICN), followed by autoradiography.

The results of the Western blot analysis are shown in FIG. 1A panel a, lower panel. Western blot analysis of cell extracts showed that high levels of OPN were expressed during the log phase of growth (FIG. 1A, panel a: lower lane 1), compared to confluent cultures (FIG. 1A, panel a: lower lane 2).

C. Immunoprecipitation

An in vitro assay was used in order to determine whether an increase in OPN gene expression is detectable. Since phorbol myristate acetate (PMA) is known to induce OPN gene expression, CASMCs were stimulated with PMA, and OPN production was detected by immunoprecipitation of cell lysates followed by Western blotting.

CASMCs were incubated with Phorbol 12-myristate 13-acetate (PMA) (250 nM) at 37° C. for 24 h. The cells were immunoprecipitated using a kit according to manufacturer's (Boehringer Mannheim) instructions. Briefly, the cells were lysed with lysis buffer, centrifuged and the supernatant incubated with rabbit OPN-antibody for 1 h then with protein A-agarose at 4° C. overnight. Bound complexes were pelleted by centrifugation, washed and electrophoresed. Western blot analysis was done as described, supra. The results are shown in FIG. 1, panel B.

In FIG. 1, panel B, left lane contains extracts from control cells which were not treated with PMA, while the right lane contains extracts from cells stimulated with 250 nM PMA. The level of OPN protein in PMA-stimulated cells was markedly higher (FIG. 1, panel B: right lane) than that of unstimulated cells (FIG. 1, panel B: left lane). The two OPN bands (right lane) detected upon PMA stimulation represent two isoforms of this protein.

D. $^{125}$I-OPN-Binding and Affinity-Crosslinking

Since OPN may exert its effect on CASMCs by interacting with its cell-surface receptor, the amount of membrane bound OPN was determined using $^{125}$I-OPN-binding and affinity-crosslinking experiments.

For binding studies, purified hOPN was radioiodinated by the Chloramine-T method (Hunter et al., (1962) Nature 194:495–496). Sub-confluent cultures of CASMCs were incubated with $^{125}$I-OPN ($3.3 \times 10^5$ cpm/well) in the absence or presence of varying concentrations of unlabeled OPN in 0.5 ml Hank's balanced salt solution (HBSS), pH 7.6, containing 0.1% BSA. After incubation at 37° C. for 3 h, the reactions were stopped by rapid removal of medium containing unbound radiolabeled OPN and the cells were washed and solubilized with 2 N NaOH. The radioactivity was measured by gamma counter and the specific binding was calculated by subtracting the non-specific binding from the total binding. The $K_d$ value was determined by Scatchard analysis using "LIGAND" computer program (Munson et al., (1980) Anal. Biochem. 107:220–239). $^{125}$I-OPN was incubated with CASMC using increasing concentrations of unlabeled OPN at 37° C. for 3 h. The results are shown in FIG. 1, panel D. The data were an average of duplicate experiments.

For affinity crosslinking experiments, sub-confluent CASMCs were incubated with $^{125}$I-OPN ($6.6 \times 10^5$ cpm/well) in 1 ml of HBSS, pH 7.6 containing 0.1% BSA in the absence or presence of unlabeled OPN or GRGDS peptide (1 $\mu$M) at 37° C. for 3 h. After washing, the cells were incubated with 0.20 mM DSS in 1 ml HBSS, pH 7.6 at 37° C. for 30 min. The cells were scraped, collected by centrifugation and lysed in 40 $\mu$l of 1% Triton X-100 solution containing 1 mM PMSF, 20 $\mu$g/ml leupeptin and 2 mM EDTA. The supernatants (30 $\mu$l) obtained by centrifugation were electrophoresed as described previously (Laemmli et al., (1970) Nature 227:680–685) and autoradiographed. The results are shown in FIG. 1, panel C.

FIG. 1, panel C, shows the results of incubation of $^{125}$I-OPN with CASMC in the absence or presence of unlabeled OPN or Gly-Arg-Gly-Asp-Ser (GRGDS) (SEQ ID NO:7) oligopeptide which corresponds to a portion of the cell adhesion sequence of OPN, and then crosslinked with disuccinimidyl suberate (DSS) (Pierce). These results show that the 300 kD protein band disappeared when the cells were pretreated with either OPN or GRGDS peptide. Furthermore, the 300 kD band was not detected in the absence of DSS.

These results indicate that OPN binds to an approximately 300 kD cell surface protein on CASMCs (FIG. 1, panel C) with high specificity and affinity (Kd=1 nM) (FIG. 1, panel D). The results of immunoprecipitation with $\alpha_v\beta_3$ integrin antibody after binding and affinity-crosslinking of $^{125}$I-OPN with CASMCs established that the approximately 300 kD protein band is indeed $\alpha_v\beta_3$ integrin.

Example 2

Influence of OPN on In Vitro Coronary Smooth Muscle Cell Migration, ECM-invasion, and Proliferation In order to determine the effects of OPN on CASMCs, prior art-accepted in vitro assay systems were used to evaluate the effects of this protein on cellular migration, ECM-invasion and proliferation as follows.

A. CASMC Migration Assay

Migration of CASMC was performed using Transwell cell culture chambers with an 8-$\mu$M pore size polycarbonate membrane (Costar) as described previously (Yue et al., (1994) Exptl. Cell Res. 214:459–464). Briefly, sub-confluent human CASMC were trypsinized, centrifuged and resuspended in basal medium (SmBM) supplemented with 0.2% BSA. This was followed by the addition of 0.25 ml of cell suspension ($5 \times 10^4$ cells) to the upper compartment of the chamber. The lower compartment contained 0.5 ml of basal medium supplemented with 0.2% BSA together with 0.68 $\mu$g/ml OPN, 1.36 $\mu$g/ml OPN, or buffer alone. After incubation at 37° C. for 24 h., the non-migrated cells on the upper surface of the filters were scraped and washed. The migrated cells were fixed in methanol, stained with Giemsa stain, counted under an inverted microscope and photomicrographed (120x) using a Zeiss photomicroscope (Axiovert 405 M). In separate experiments, cells in the upper compartment were also treated with monoclonal mouse anti-human $\alpha_v\beta_3$-antibody (Chemicon) (10 $\mu$g/ml) before being assayed for migration in order to ascertain whether this OPN-stimulated migration is mediated via $\alpha_v\beta_3$. Preimmune IgG treatment served as a non-specific control. The results are shown in FIG. 2A.

FIG. 2A shows that the rate of migration of CASMCs was enhanced with increasing concentrations of OPN used as chemoattractant. Additionally, the OPN-induced migration was blocked when the cells were pre-treated with $\alpha_v\beta_3$ integrin-antibody prior to performing each of these assays. A pre-immune IgG, used as a control, failed to exert any inhibitory effect on OPN-induced migration.

B. ECM-Invasion Assay

The ECM-invasion assay was performed using a commercially available 24-well matrigel-coated invasion chamber (Collaborative Research) as described previously (Kundu et al., (1996) Proc. Natl. Acad. Sci. (USA) 93:2915–2919). Briefly, the confluent CASMC were trypsinized, centrifuged, and resuspended in basal medium supplemented with 0.1% BSA. The lower compartment of the invasion chamber was filled with fibroblast-conditioned medium (FCM) which served as a chemoattractant. The invasion assays were initiated by inoculating the upper chamber with cells ($1 \times 10^5$/well) which were either untreated or treated with varying concentrations of OPN (0.5–2.0 $\mu$g/ml). After incubating at 37° C. for 24 h, the cells in the upper chamber were discarded, the matrigel was scraped clear and the cells which had invaded the matrigel and migrated to the lower surface of the filter, were fixed, stained, counted and photomicrographed (120x) as described above. The cells were also pre-treated with mouse anti-human $\alpha_v\beta_3$ antibody (Chemicon) (10 $\mu$g/ml) as described above to determine if the OPN-induced invasion was mediated via $\alpha_v\beta_3$. Preimmune IgG was used as a non-specific control. The results are shown in FIG. 2B.

The results show that OPN-treatment of the cells enhanced their invasiveness (FIG. 2B) when tested on "MATRIGEL," an artificial ECM, in a dose-dependent manner. The OPN-induced ECM-invasion was blocked when the cells were pre-treated with $\alpha_v\beta_3$ integrin-antibody prior to performing each of these assays. A pre-immune IgG, used as a control, failed to exert any inhibitory effect on OPN-induced ECM-invasion.

C. CASMC Proliferation Assay

Proliferation studies were carried out in the presence of platelet-derived growth factor-AB (PDGF-AB) as it has been suggested that in vivo platelet activation may contribute to the pathogenesis of restenosis. CASMCs were cultured as described above and the cells were starved in serum free media for 48 h. The proliferation assays were performed as described previously (Monfardini et al., (1995) J. Biol. Chem. 270:6628–6638). Briefly, the cells were incubated in the absence or presence of PDGF-AB (100 ng/ml) (Upstate Biotechnology, Lake Placid, N.Y.) and increasing concentrations of OPN (1.0–6.0 µg/ml) at 37° C. for 24 h. In separate experiments, cells were pre-treated with either mouse anti human $\alpha_v\beta_3$-antibody (5 µg/ml), preimmune IgG or GRGDS peptide (10 nM) followed by OPN (3.0 µg/ml). After 4 h, [3H]thymidine (1 µCi/ml) was added and the cells were maintained in culture for an additional 24 h under the same culture conditions as described previously. After removing the supernatants, the cells were washed with basal medium and lysed in 50% TCA. The acid precipitable cell-bound radioactivity was measured using a scintillation counter (Beckman). The results are shown in FIG. 2C.

FIG. 2C shows that OPN-treatment of CASMCs also stimulated their proliferation in a dose-dependent manner. While PDGF-AB alone had virtually no effect on CASMC proliferation, treatment of these cells with OPN had a dramatic dose-dependent effect when used in conjunction with 100 ng/ml of PDGF-AB (FIG. 2C). Treatment of the cells with OPN alone yielded a modest proliferative response.

Interestingly, treatment of CASMCs with Gly-Arg-Gly-Asp-Ser (GRGDS) oligopeptide, or with $\alpha_v\beta_3$ antibody drastically inhibited OPN-induced proliferation (FIG. 2C).

Taken together, these results indicate that OPN gene expression is enhanced in proliferating, compared to contact-inhibited CASMCs, and that treatment of these cells with purified OPN stimulated their motility, ECM-invasion, and proliferation. Moreover, these effects of OPN are transduced via $\alpha_v\beta_3$ integrin. Importantly, these data also suggest that OPN-antisense sequences may be useful for the inhibition of OPN-mediated effects.

Example 3

OPN mRNA and Protein Expression in Human Coronary Atherectomy Tissues

The above-discussed data obtained from in vitro investigations on cultured CASMCs raised the possibility that CASMCs which are located in vivo on the arterial wall migrate from that location, invade the ECM, and proliferate to cause the occlusion which is associated with the restenosis observed following DCA.

Two questions, on which the prior art is silent, were particularly important. The first was whether a distinction could be made between atherosclerotic and non-atherosclerotic coronary arterial tissues solely on the basis of OPN-mRNA and protein expression patterns. If such was the case, the second question was whether the arterial tissues which produce OPN also express one of its receptors, the $\alpha_v\beta_3$ integrin. These questions were addressed by the determination of the expression of OPN-mRNA, OPN protein and $\alpha_v\beta_3$ integrin protein in control and coronary atherectomy tissues from human subjects.

A. Atherosclerotic Tissue Expresses $\alpha_v\beta_3$ Integrin Protein and Higher Levels of OPN-mRNA and OPN Protein than Control Tissue Coronary atherectomy tissues was obtained from 13 DCA-patients i.e., patients who participated in an approved clinical research protocol and in whom directional coronary atherectomy (DCA) was clinically indicated. Informed consent was obtained from all patients in whom atherectomy/angioplasty was clinically indicated. Autopsy specimens of normal coronary arteries from 6 subjects (ages 18–68) at autopsy who died of non-cardiac causes and had no evidence of atherosclerosis served as controls. A summary of profiles of patient and control subjects is presented in Table 1.

TABLE 1

| Profile of Patients* and Controls** | | |
|---|---|---|
| Number of Patients | Age Range | Sex |
| 13 (DCA-patients) | 43–62 | 2 F |
| | | 11 M |
| 6 (Controls) | 18–68 | 2 F |
| | | 4 M |

*Informed consent was obtained after the nature and possible consequences of the atherectomy procedure were explained.
**No evidence of coronary atherosclerosis at autopsy: death due to non-cardiac causes.

DCA-patient and control tissues were used to detect OPN-mRNA by in situ hybridization and RT-PCR, $\alpha_v\beta_3$ integrin protein by immunofluorescence, and OPN protein by both immunofluorescence and Western blotting. The atherectomy tissue samples, immediately after removal, were divided aseptically into three parts for RNA extraction, Western blot analysis and in situ hybridization, respectively. RNAse-free equipments and reagents were used for collection and storage of tissues used for in situ hybridization and RNA extraction. Control samples obtained at autopsy were prepared under the same conditions.

1. In situ Hybridization

For in situ hybridization, a digoxigenin-labeled oligonucleotide probe derived from the sequence of human OPN cDNA (FIG. 5, SEQ ID NO:15) was used as follows. Sections of paraformaldehyde-fixed tissues were placed on ribonuclease-free polylysine-treated glass slides (American Histolabs, Inc.) and in situ hybridization was carried out as previously described [Peri et al. (1995) J. Clin. Invest. 96:343–353]. The hOPN probe, hOPN-P$_2$ (nt 647–608): 5'-TCC ATG TGT GAG GTG ATG TCC TCG TCT GTA GCA TCA GGG T-3') (SEQ ID NO:8), was 3' end-labeled with digoxigenin-11-ddUTP (Boehringer Mannheim) as described previously [Peri et al. (1993) J. Clin. Invest. 92:2099–2109]. The slides were photomicrographed with a Zeiss Axiomat photomicroscope (magnification 400×). The results of in situ hybridization are shown in FIG. 3A.

FIG. 3A, panels a & b and c & d are bright field photomicrographs of coronary atherectomy and normal coronary artery tissues, respectively. In situ hybridization with an OPN probe showed that atherosclerotic tissues obtained from DCA-patients expressed very high levels of OPN-mRNA while it was virtually undetectable in control samples.

2. Reverse Transcription Polymerase Chain Reaction

For RT-PCR, reverse transcription of total RNAs from DCA-patients and controls and cDNA amplifications were performed according to the method described previously (Peri et al., (1993) J. Clin. Invest. 92:2099–2109) using the primers described supra. The results are shown in FIG. 3B. In FIG. 3B, panel a, lane S contains RNA from human kidney (Clontech, CA) which was used as a positive control since kidney is known to constitutively synthesize high levels of OPN. Lanes 1–5 contain RNA from autopsy samples of 5 representative control subjects without evidence of coronary artery disease. OPN-mRNA and GAPDH-mRNA are shown (panels a and b).

The results of RT-PCR using total RNA from control (FIG. 3B, panel a: lanes 1–5) and patient samples (FIG. 3B, panel b: lanes 1–5) corroborated the in situ hybridization results (FIG. 3A, panels a–d); while OPN-mRNA signal was virtually absent in control tissue, significant levels of OPN-mRNA were detected in tissue from coronary atherectomy samples. The apparent lack of OPN-mRNA in control (autopsy) coronary arteries was not due to degradation of nucleic acids since the strong RT-PCR amplification of mRNA of a house keeping gene, GAPDH, was virtually identical in each of these samples (FIG. 3B, bottom, panels a & b).

3. Immunofluorescence

In order to determine whether the outer (adventitia), middle (media) or the inner (intima) tissue layers of the coronary arteries expressed OPN and $\alpha_v\beta_3$ integrin, immunofluorescence was performed on both DCA-patient and control tissues using antibodies against OPN (Chacklaparampil et al., (1996) Oncogene 12:1457–1467), human SMC-specific α-actin monoclonal antibody (clone 1A4) (Sigma), and human $\alpha_v\beta_3$ integrin (Chemicon). Both SMC-specific α-actin and $\alpha_v\beta_3$ integrin were readily detectable in both patients and controls, and the intensity of SMC-specific α-actin and $\alpha_v\beta_3$ integrin was also very similar in both controls and patients. In contrast, patient tissues produced a high level of OPN-specific immunofluorescence, while OPN-immunofluorescence was virtually undetectable in the control tissues.

These results demonstrate that control and atherosclerotic tissues express $\alpha_v\beta_3$ integrin protein and that OPN protein levels are elevated in atherosclerotic tissue. Furthermore, these data also show that expression of OPN and $\alpha_v\beta_3$ integrin is specific to the smooth muscle layer of coronary arteries of both control and atherosclerotic patients.

4. Western Blotting

Western blot analysis was performed as described supra in Example 1, and the results are shown in FIG. 3C. In FIG. 3C, panel a shows autopsy samples from 5 apparently normal coronary arteries (lanes 1–5). Panel b shows samples from 5 atherectomy patients (lanes 1–5). Lane S in panels a and b contains purified OPN prepared from human milk as previously described [Senger et al. (1996) supra] which was used as a standard. The results of the Western blot analysis showed a virtual lack of OPN in control tissues (panel a: lanes 1–5) compared to the detection of appreciable levels of OPN in atherectomy samples (panel b: lanes 1–5). The SDS-PAGE and Western blotting of patient tissue extracts revealed two distinct OPN bands as noted above (see FIG. 1A).

B. Plasma OPN Levels are Dramatically Elevated Following Angioplasty

Since significantly elevated OPN levels were detected in atherosclerotic tissue as shown supra, and since OPN is a secreted protein, the effect of DCA on OPN levels in blood plasma was investigated. This was achieved by Western blot analysis of blood samples collected from DCA patients on the day before the procedure, 24 h after, and at weekly intervals for 4 weeks following DCA. Plasma samples which were prepared for OPN detection as previously described (Senger et al., (1988) Cancer Res. 48:5770–5774) were used for Western blotting using the method described in Example 1, supra. Equal amounts of total plasma proteins were loaded in each lane for electrophoresis. Semi-quantitative, densitometric analysis of the OPN bands in Western blots was performed using an LKB Ultrascan LX-800 densitometer. Plasma samples from healthy individuals, who had no clinical evidence of coronary artery disease, served as controls. The results of the Western blot analysis are shown in FIG. 4.

Figure 4A:
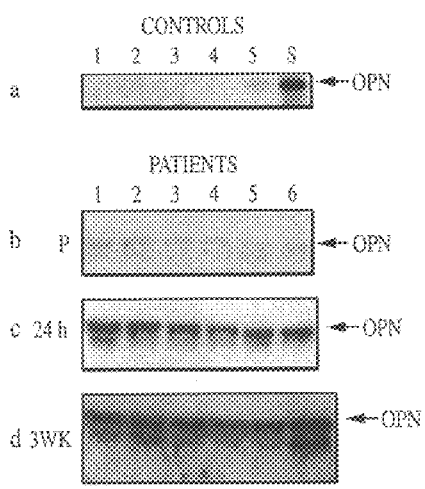
FIG. 4 shows (A) Western blot analysis of OPN in plasma samples of normal controls (panel a) and atherectomy patients (panels b, c, and d); (B) densitometric analysis of plasma OPN bands from normal controls ($C_{1-3}$), atherectomy patients before DCA (P); and atherectomy patients after 1–4 weeks of DCA.

In FIG. 4A, panel a, lanes 1–5 contain plasma samples from 5 different control patients containing equal amounts of protein as determined by spectrophotometric determination; lane S contains purified OPN standard. FIG. 4A, panel b, lanes 1–6 contain plasma samples from DCA patients obtained 24 h before the procedure; panel c, lanes 1–6 contain plasma samples from DCA patients 24 h after the procedure; panel d contains plasma samples from DCA patients obtained 3 weeks after DCA.

The results in FIG. 4A showed a dramatic difference in the levels of plasma OPN between controls and DCA patients. Importantly, as shown in panel a, the control plasma samples had virtually undetectable levels of OPN (lanes 1–5), whereas, those from DCA patients, collected 24 h before the procedure (P, panel b), had readily visible OPN bands (lanes 1–6). Significantly, plasma OPN levels dramatically increased 24 h after DCA (panel c) and remained elevated even 3 weeks after the procedure (panel d).

Figure 4B:
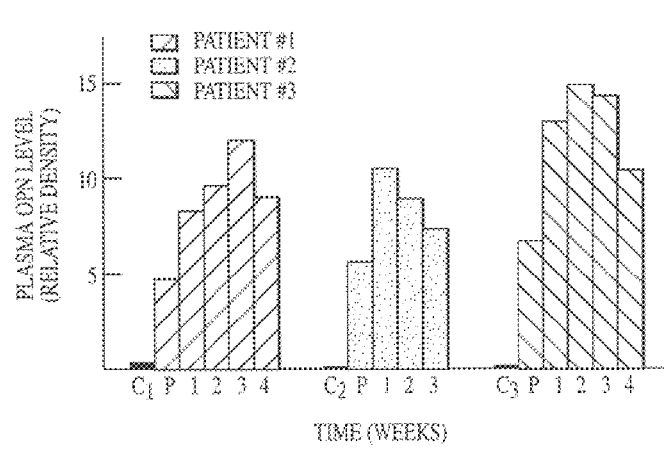

Data obtained from a followup of relative densities of OPN bands, resolved by SDS-PAGE and Western blotting of plasma samples of three representative DCA patients, collected over a 4 week period, is shown in FIG. 4B. In FIG. 4B, plasma samples were obtained from controls ($C_1$, $C_2$, and $C_3$) and patients 24 h before DCA (P). The numbers indicate the time in weeks after the procedure.

Surprisingly, the baseline plasma OPN levels of the patients, even before the procedure, were remarkably higher than those of the healthy controls. Moreover, plasma OPN levels showed a significant increase within 24 h following DCA, and these elevated plasma OPN levels were sustained for at least 4 weeks after DCA.

Taken together, the data unambiguously demonstrate (a) expression of $\alpha_v\beta_3$ integrin protein in CASMCs in the arteries of control and atherosclerotic patients [as detected by immunofluorescence], (b) remarkable elevation in the expression of OPN-mRNA [as detected by in situ hybridization and RT-PCR] and OPN protein [as detected by visual inspection and densitometric analysis of Western blots] in CASMCs in the arteries of patients suffering from coronary atherosclerosis as compared to healthy individuals, (c) remarkable sustained elevation of OPN protein levels in the serum of arterial atherosclerotic patients following DCA procedure as compared to the levels in healthy controls and to atherosclerotic patients who did not undergo DCA.

Example 4

In Vitro Lipofection of Human Coronary Artery Smooth Muscle Cells with Antisense OPN Sequences In order to determine the efficacy of antisense OPN oligonucleotides in the treatment of restenosis, antisense oligonucleotides designed to bind to mRNA encoded by the human OPN gene sequence were synthesized as phosphorothioate-oligonucleotides and their effect in vitro on the migration and proliferation of human coronary arterial smooth muscle cells, and on the expression of OPN in these cells was determined.

A. Design and Synthesis of Antisense OPN Sequences

Five antisense OPN sequences were designed to bind to sequences within the coding region of the human OPN gene sequence depicted in FIG. 5 as follows: ASHOPN-P1: 5'-AATCACTGCAATTCTCATGG-3' (SEQ ID NO:9), ASHOPN-P2: 5'-TTAACTGGTATGGCACAGGT-3' (SEQ ID NO:10); ASHOPN-P3: 5'-AGAACTTCCAGAATCAGCCT-3' (SEQ ID NO:11); ASHOPN-P4: 5'-TCGTTGGACTTACTTGGAAG-3' (SEQ ID NO:12); and ASHOPN-P5: 5'-ATGCTCATTGCTCTCATCAT-3' (SEQ ID NO:13). For each of the antisense sequences, a corresponding control sense sequences was also designed. For the antisense ASHOPN-P1, the corresponding control sense sequence was SHOPN-P6: 5'CCATGAGAATTGCAGTGATT-3' (SEQ ID NO:14). The antisense and sense sequences were synthesized as phosphorothioate-oligonucleotides by GIBCO-BRL (Life Technologies), Gaithersburg, Md.

B. In Vitro Lipofection

Human coronary artery smooth muscle cells (CASMCs) (Clonetics) were subjected to lipofection with the antisense sequence ASHOPN-P1 or with the control sense sequence SHOPN-P6, and the effect of lipofection was measured on the proliferation of the lipofected cells and on the expression of OPN as measured by Western blot analysis.

CASMCs (Clonetics) were transfected with a "LIPOFECTIN"-oligonucleotide complex according to the manufacturer's (GIBCO-BRL Life Technologies, Inc. Gaithersburg, Md.) specifications. Briefly, 5 µg of "LIPOFECTIN" was mixed with either 1 or 2 µg of antisense oligonucleotide in 200 µl of serum free medium (SFM) (also called basal medium) and incubated at room temperature for 15 min. Cells ($1 \times 10^5$ cells/well, 12-well plate) during log phase of growth were washed with SFM and 1 ml of SFM containing Lipofectin with different amounts of antisense S-oligonucleotides was added to each well and mixed by gentle agitation. The cells were incubated further with the same medium at 37° C. for 12 h. Additional control cells which received either SFM, or SFM which contained "LIPOFECTIN" alone, were also included. At the end of the 12 h incubation period, cell viability was detected by trypan blue dye exclusion test which showed the cells were healthy. The SFM medium containing "LIPOFECTIN"-oligonucleotide complex was removed, and the cells incubated for an additional 48 h in regular medium. At the end of this incubation period, the cells were ready for the determination of a dose response on OPN expression as measured by Western blotting.

C. Effect of Lipofection with Antisense OPN Sequences on Migration, Invasion of ECM, Proliferation and OPN Expression The effect of antisense ASHOPN-P1 on the proliferation of human coronary artery smooth muscle cells (CASMCs) was determined as described supra. Briefly, CASMCs which had been transfected with "LIPOFECTIN" alone, or in the presence of either OPN sense or OPN antisense oligonucleotides (1 µg each) as described above were incubated further using PDGF-AB (100 ng/ml) in the presence or absence of OPN (3 µg/ml) containing basal medium (SFM) for 24 h. After 4 h, [3H]-thymidine (1 mCi/ml) was added and the cells were maintained in culture for an additional 24 h under the same culture conditions. The supernatant was removed and the cells washed in basal medium (SFM) and lysed in 50% TCA. The acid precipitable radioactivity was measured using a scintillation beta counter (Beckman). The results of the proliferation assay are shown in FIG. 6.

Figure 6:
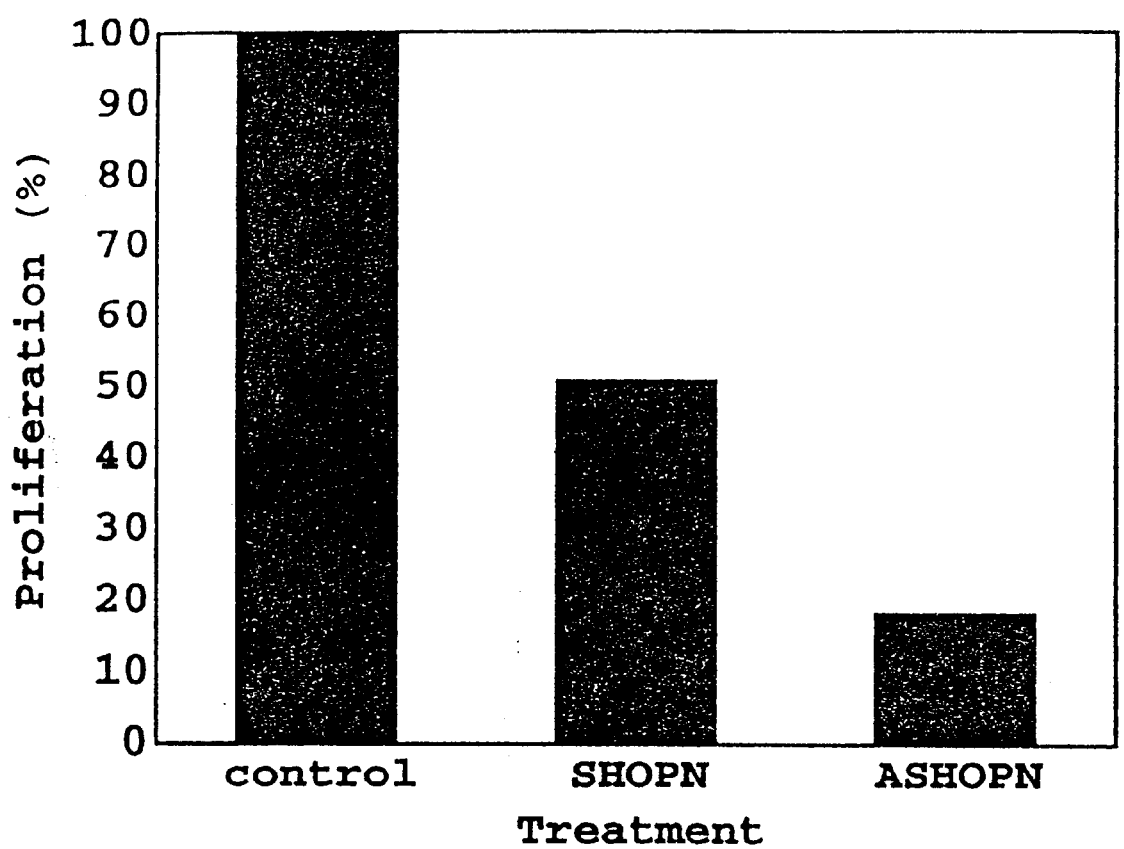
FIG. 6 shows the effect of "LIPOFECTIN" alone (control), or in the presence of OPN sense sequence SHOPN-P2 (SHOPN) or the antisense sequence ASHOP-P1 (ASHOPN) on the proliferation of human coronary artery smooth muscle cells.

FIG. 6 shows the effect of treatment of human CASMCs with "LIPOFECTIN" (5µg/200 µl) alone (control), or in the presence of sense sequence, SHOPN-P6 (1.5 µg/200 ml) or antisense sequence, ASHOPN-P1 (1.5 µg/200 µl). The results in FIG. 6 show that treatment with the antisense ASHOPN-P1 sequence resulted in an 82% inhibition of cell proliferation as compared to cells treated with "LIPOFECTIN" alone, whereas cells treated with the sense sequence, SHOPN, showed about 50% inhibition of proliferation.

Figure 7:
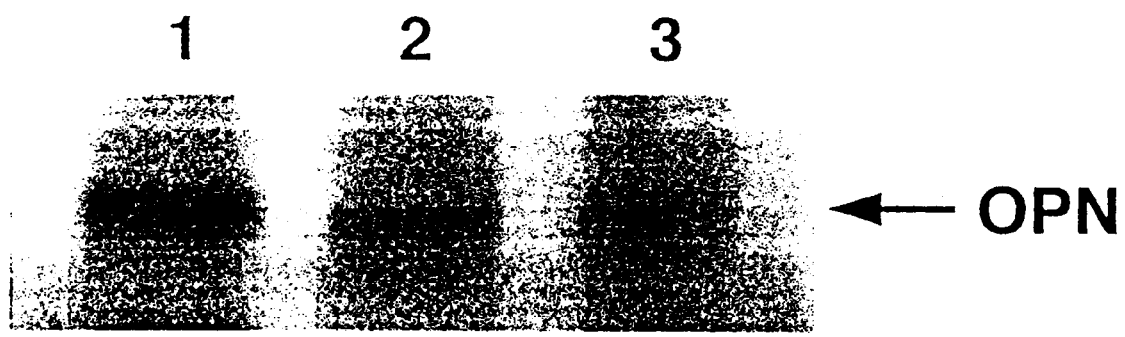
FIG. 7 shows the effect of transfection of CASMCs with "LIPOFECTIN" alone, or "LIPOFECTIN" containing different concentrations of S-oligonucleotide antisense sequence ASHOPN-P1 (ASHOPN) (SEQ ID NO:9) on OPN-protein production as determined by immunoprecipitation followed by Western blot analysis.

The effect of antisense OPN sequences on OPN expression was determined by Western blot analysis as described above. FIG. 7 shows the expression of OPN when cells were treated with "LIPOFECTIN" alone or two different doses of S-oligonucleotides antisense OPN sequences (lanes 1–3). Lane 1 contains immunoprecipitates of cells treated with "LIPOFECTIN" alone; Lane 2 contains immunoprecipitates of cells treated with 1 µg S-oligonucleotide ASHOPN-P1 (ASHOPN); and Lane 3 contains immunoprecipitates of cells treated with 2 µg S-oligonucleotide ASHOPN-P1 (ASHOPN).

The results demonstrate that the antisense sequence ASHOPN-P1 was capable of inhibiting expression of OPN by CASMCs and resulted in the inhibition of CASMC proliferation and OPN protein expression as compared to either "LIPOFECTIN"-treated cells or to OPN sense-treated cells. Moreover, these results demonstrate that the effect of antisense sequence ASHOPN-P1 is specific.

Example 5

Testing Antisense OPN Sequences in a Rat Carotid Artery In Vivo Model System

The effect of antisense OPN sequences on restenosis is investigated in an art-accepted rat carotid artery in vivo model by local administration of antisense OPN sequences to arteries which had been traumatized by catheterization, followed by the assessment of the effect of treatment on OPN expression and restenosis.

A. Administration of Antisense OPN to Traumatized Rat Carotid Artery

Antisense OPN sequences are administered to traumatized rat carotid arteries via lipofection or as part of a pluronic gel. Traumatization of the rat carotid artery is an art-accepted method for investigating restenosis [Lee et al. (1993) Circulation Research 73:797–807; von der Leyen et al. (1994) FASEB J. 8:A802; Simons et al. (1992) Nature 359:67–70 (1992); Edelman et al. (1992) J. Clin,. Invest. 89:465–473; Morishita et al. (1993) Proc. Natl. Acad. Sci. USA 90:8474–8478].

1. Lipofection

In order to traumatize rat arteries, the adventitia of the carotid artery are stripped as previously described [Simons et al. (1992) Nature 359:67–70 (1992); Edelman et al. (1992) J. Clin,. Invest. 89:465–473; Morishita et al. (1993) Proc. Natl. Acad. Sci. USA 90:8474–8478] by subjecting the left common carotid arteries of rats to balloon angioplasty which denudes endothelium and induces a highly reproducible intimal migration/proliferation of SMCs over the entire length of the affected blood vessel. Briefly, male Sprague-Dawley rats (average weight 500 g) (Charles Rivers) are anaesthetized with Nembutal (4 mg per 100 g), and the left carotid artery of each animal is isolated by a midline cervical incision, suspended on ties and stripped of adventitia. A 2F Fogarty catheter is introduced through the external carotid artery of each rat, advanced to the aortic arch, the balloon is inflated to produce moderate resistance to catheter movement and then gradually withdrawn to the entry point. The entire procedure is repeated three times for each animal. After vascular injury to the carotid artery, the distal injured segment is transiently isolated by temporary ligatures. The oligonucleotide-"LIPOFECTIN" complex (prepared as described supra) is infused into the segment and incubated for 15 min at room temperature. After a 15-min incubation, the infusion cannula is removed, and blood flow to the carotid artery is restored by release of the ligatures. Controls receive either "LIPOFECTIN" alone, or a complex of a corresponding sense oligonucleotide-"LIPOFECTIN".

2. Pluronic Gel

After vascular injury of the carotid artery, the antisense OPN oligonucleotide sequences are added at a concentration of 1 mg ml$^{-1}$ to 25% (w/v) solutions of F127 pluronic gels prepared following the manufacturer's (BASF Wyandotte Corporation) instructions, and maintained at 4° C. Prechilled pipettes and tips are used to apply a 200 μl solution to the carotid artery from which the adventitia is stripped. On contact with tissues at 39° C., the solution gels instantaneously generating a translucent layer that envelops the treated region. The wounds are closed immediately after application of the gel, and the rats are returned to their cages. Inspection of additional animals is expected to reveal that pluronic gel disappears over 1–2 h. Controls receive either pluronic gel alone, or pluronic gel containing a corresponding sense sequence.

B. Effect of Treatment with Antisense OPN on OPN Expression

The effect of antisense treatment on expression of OPN mRNA is determined by Northern analysis of the expression of the previously-described rat osteopontin cDNA sequence (Oldberg et al. (1986) Proc. Natl. Acad. Sci. USA 83:8819–8823) (SEQ ID NO:16) shown in FIG. 8.

The effect of antisense OPN oligonucleotides in suppressing OPN mRNA levels in the rat carotid artery is investigated 2 weeks after injury when the extent of SMC accumulation has reached a maximum. The treated portion of the blood vessel is surgically removed from five pairs of antisense- and sense-treated rats. It is expected that injured carotid artery treated with antisense oligonucleotide exhibits lowered, or undetectable, levels of OPN mRNA as compared to injured carotid artery treated with sense oligonucleotide.

The effect of antisense treatment on expression of OPN protein is also determined by Western blot analysis according to methods known in the art (Singh et al. (1990) J. Biol. Chem. 265:18696–18701; Chakalaparampil et al. (1996) Oncogene 12:1457–1467). For Western blot analysis, the treated portion of the blood vessel is surgically removed, and prepared for Western blotting as described above, with the exception that antibody which recognizes rat osteopontin, rather than human osteopontin, is used. Antibodies which are cross-reactive with rat osteopontin include the previously-described anti-OPN serum (OST-1) as well as the commercially available anti-fibronectin serum (Collaborative Research). OST-1 was raised against the synthetic oligopeptide NH$_2$-DPKSKEDDRYLKFRIS-COOH (SEQ ID NO:18), which represents amino acid residues 291–306 of rat OPN (Singh et al. (1990) J. Biol. Chem. 265:1869–1870). OST-1 is cross-reactive with both mouse and human OPNs (Singh el al. (1992) J. Biol. Chem. 267:2384–2385). For immunoprecipitation of proteins, aliquots containing equal amounts of trichloroacetic acid-precipitated protein is diluted with 1 volume of RIPA buffer (0.05 M Tris-HCl (pH 7.2), 0.15 M NaCl, 1% Triton X-100, 1% sodium deoxycholate, 0.1% SDS, 100 Kalikrein inactivating units of aprotinin/ml, 5 mM PMSF and 5 μg/ml of trypsin inhibitor) and incubated at 4° C. for 2 h with 15 μl of anti-fibronectin or 25 μl of OST-1. The resulting immune complexes are collected by adding an excess (30 μl of 50% slurry in RIPA buffer) of protein A-Sepharose (Pharmacia Biotechnology, Inc.) to the reaction mixture and incubating for 1 h at 4° C. with gentle agitation. The adsorbed immune complexes are pelleted by centrifugation, washed three times with RIPA buffer, twice with PBS, and finally rinsed with distilled water. The immunoprecipitated proteins, s are subsequently suspended in 50 μl of sample buffer (0.07 M Tris-HCl (pH 6.8), 3% SDS, 5% β-mercaptoethanol, 10% glycerol, and 0.01% bromophenol blue). To denature osteopontin-fibronectin complexes, samples readjusted to 0.2% SDS, incubated at 95° C. for 5 min, diluted with 1 volume of RIPA buffer lacking SDS, and immunoprecipitated with either OST-1 or anti-fibronectin serum. Electrophoretic analysis by SDS-PAGE is then carried out on 10% slab gels.

It is expected that the levels of OPN in injured vessels treated with antisense will be reduced as compared with OPN levels in injured vessels which have received no treatment or which are treated with carrier (Le., "LIPOFECTIN" or pluronic gel) alone or with a sense oligonucleotide/carrier complex.

C. Effect of Treatment with Antisense OPN on Restenosis

The effect of antisense OPN oligonucleotides on restenosis is determined by measurement of vascular DNA synthesis and content, and of the effect on neointimal size.

1. Measurement of DNA Synthesis

For bromodeoxyuridine (BrdUrd) staining, BrdUrd is injected into rats after vascular injury (100 mg/kg subcutaneously and 30 mg/kg Intraperitoneally at 18 h prior to sacrifice and then 30 mg/kg intraperitoneally at 12 h prior to sacrifice). Rats are sacrificed on day 4 after the surgical procedure. The carotid artery is removed after perfusion-fixation (110 mmHg; 1 mmHg=133 Pa) with 4% (wt/vol) paraformaldehyde and processed for immunohistochemistry by using anti-BrdUrd antibodies (Amersham). The proportion of BrdUrd-positive cells is determined by cell counts under light microscopy in a blinded fashion. Measurement of DNA is performed at 4 days after the surgical procedure using bisbenzimide trihydrochloride (Pierce). It is expected that antisense treatment of injured arteries will inhibit BrdUrd incorporation (a marker of DNA synthesis and cell proliferation) in the vessel wall as compared to the sense-treated controls or to the untreated injured control vessels.

2. Morphometric Analysis

Formation of neointima along the length of the treated artery is determined at 2, 4, and 8 weeks after the surgical procedure. At the time of killing, the animals are anaesthetized with Nembutal and perfused with 150 cc normal saline under a pressure of 120 mm Hg. The carotid arteries are removed, fixed in 3% formalin, and processed for light microscopy in a standard manner. Three individual sections from the middle of surgically treated segments which are treated with antisense sequences are analyzed by measuring the mean cross-sectional areas of the intimal and of the medial regions which are untreated, treated with carrier (i.e., pluronic gel or "LIPOFECTIN") alone, treated with carrier plus antisense oligonucleotide, or treated with carrier plus sense oligonucleotide. These measurements are used to determine a ratio of intimal to medial cross-sectional areas. In addition, three sections from the middle section of the injured region which has not received antisense treatment are also analyzed. Animals are coded so that operation and analysis are performed without knowledge of which treatment individual animals receive. It is expected that treatment with antisense will result in a reduction of the cross-sectional ratio of intima/media as compared with the cross-sectional ratio of intima/media in control injured arteries receiving no treatment, carrier alone, or a carrier/sense oligonucleotide complex.

In order to determine the selectivity of the antisense effect, a dose response (e.g., 1 $\mu$M–20 $\mu$M antisense) of the effect on the intimal/medial cross-sectional ratio is determined at the site of oligonucleotide administration. Additionally, the selectivity of the antisense effect is determined by measuring the intimal/medial cross-sectional ratio along the length of the treated vessel in which the site of oligonucleotide administration is marked with silk ties. It is expected that the intimal/medial cross-sectional ratio in injured vessels treated with antisense will be reduced as compared with the ratio in injured vessels which have received no treatment or which are treated with carrier (i.e. "LIPOFECTIN" or pluronic gel) alone or with a sense oligonucleotide/carrier complex. Such a reduction in ratio indicates that the antisense molecule is useful in reducing restenosis in a human subject.

As clear from the data presented herein, the present invention has the advantage of providing methods and compositions for preventing and/or treating restenosis. In particular, the OPN antisense sequences are useful in preventing the development of restenosis in angioplasty procedures. Furthermore, OPN antisense sequences provide a tool for specific therapy with minimal potential adverse side-effects in view of the ability of the sequences specifically to target expression of a single gene which is implicated in the development of restenosis. Moreover, OPN antisense sequences as disclosed herein are easy to administer and are effective over a short period of time.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method of diminishing osteopontin expression, comprising:
   a) providing:
      i) a human smooth muscle cell in culture; and
      ii) an osteopontin antisense oligonucleotide complementary to a polynucleotide selected from the group consisting of SEQ ID NO:9, SEQ ID NO:10, SEQ ID NO:11, SEQ ID NO:12, and SEQ ID NO:13; and
   b) administering an amount of said oligonucleotide to said smooth muscle cell in culture under conditions such that said osteopontin expression is diminished.

2. The method of claim 1, wherein said human smooth muscle cell is a coronary artery smooth muscle cell.

3. The method of claim 1, wherein said osteopontin antisense oligonucleotide comprises one or more phosphorothioate linkages.

4. The method of claim 1, wherein said osteopontin antisense oligonucleotide is entrapped in a liposome.

5. A method of reducing human smooth muscle cell proliferation, comprising:
   a) providing:
      i) a human smooth muscle cell in culture; and
      ii) an osteopontin antisense oligonucleotide complementary to a polynucleotide selected from the group consisting of SEQ ID NO:9, SEQ ID NO:10, SEQ ID NO:11, SEQ ID NO:12, and SEQ ID NO:13; and
   b) administering an amount of said oligonucleotide to said human smooth muscle cell under conditions such that proliferation of said human smooth muscle cell is diminished.

6. The method of claim 5, wherein said osteopontin antisense oligonucleotide comprises one or more phosphorothioate linkages.

7. The method of claim 6, wherein said osteopontin antisense oligonucleotide is entrapped in a liposome.

* * * * *

SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
ctacaaccag catatcttca                                                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
caccagtctg atgagtctca                                                    20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
tccatgtgtg aggtgatgtc                                                    20

<210> SEQ ID NO 4
<211> LENGTH: 18
<212> TYPE: DNA
<213> ORGANISM: Artificial Sequence
<220> FEATURE:
<223> OTHER INFORMATION: Synthetic

```
<400> SEQUENCE: 4
ccatggagaa ggctgggg                                                   18

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
caaagttgtc atggatgacc                                                 20

<210> SEQ ID NO 6
<211> LENGTH: 19
<212> TYPE: DNA
<213> ORGANISM: Artificial Sequence
<220> FEATURE:
<223> OTHER INFORMATION: Synthetic

<400> SEQUENCE: 6
ctaagcagtt ggtggtgca                                                  19

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Gly Arg Gly Asp Ser
1               5

<210> SEQ ID NO 8
<211> LENGTH: 40
<212> TYPE: DNA
<213> ORGANISM: Artificial Sequence
<220> FEATURE:
<223> OTHER INFORMATION: Synthetic

<400> SEQUENCE: 8
tccatgtgtg aggtgatgtc ctcgtctgta gcatcagggt                           40

<210> SEQ ID NO 9
<211> LENGTH: 20
<212> TYPE: DNA
<213> ORGANISM: Homo sapiens

<400> SEQUENCE: 9
aatcactgca attctcatgg                                                 20

<210> SEQ ID NO 10
<211> LENGTH: 20
<212> TYPE: DNA
<213> ORGANISM: Homo sapiens

<400> SEQUENCE: 10
ttaactggta tggcacaggt                                                 20

<210> SEQ ID NO 11
<211> LENGTH: 20
<212> TYPE: DNA
<213> ORGANISM: Homo sapiens
```

-continued

```
<400> SEQUENCE: 11
agaacttcca gaatcagcct                                                    20

<210> SEQ ID NO 12
<211> LENGTH: 20
<212> TYPE: DNA
<213> ORGANISM: Homo sapiens

<400> SEQUENCE: 12
tcgttggact tacttggaag                                                    20

<210> SEQ ID NO 13
<211> LENGTH: 20
<212> TYPE: DNA
<213> ORGANISM: Homo sapiens

<400> SEQUENCE: 13
atgctcattg ctctcatcat                                                    20

<210> SEQ ID NO 14
<211> LENGTH: 20
<212> TYPE: DNA
<213> ORGANISM: Homo sapiens

<400> SEQUENCE: 14
ccatgagaat tgcagtgatt                                                    20

<210> SEQ ID NO 15
<211> LENGTH: 1422
<212> TYPE: DNA
<213> ORGANISM: Homo sapiens

<400> SEQUENCE: 15
gaccagactc gtctcaggcc agttgcagcc ttctcagcca aacccgacca aggaaaactc        60
actaccatga gaattgcagt gatttgcttt tgcctcctag gcatcacctg tgccatacca       120
gttaaacagg ctgattctgg aagttctgag gaaaagcagc tttacaacaa atacccagat       180
gctgtggcca catggctaaa ccctgaccca tctcagaagc agaatctcct agccccacag       240
aatgctgtgt cctctgaaga aaccaatgac tttaaacaag agacccttcc aagtaagtcc       300
aacgaaagcc atgaccacat ggatgatatg gatgatgaag atgatgatga ccatgtggac       360
agccaggact ccattgactc gaacgactct gatgatgtag atgacactga tgattctcac       420
cagtctgatg agtctcacca ttctgatgaa tctgatgaac tggtcactga ttttcccacg       480
gacctgccag caaccgaagt tttcactcca gttgtcccca cagtagacac atatgatggc       540
cgaggtgata gtgtggttta tggactgagg tcaaaatcta gaagtttcg cagacctgac       600 atccagtacc ctgatgctac agacgaggac atcacctcac acatggaaag cgaggagttg       660
aatggtgcat acaaggccat ccccgttgcc caggacctga acgcgccttc tgattgggac       720
agccgtggga aggacagtta tgaaacgagt cagctggatg accagagtgc tgaaacccac       780
agccacaagc agtccagatt atataagcgg aaagccaatg atgagagcaa tgagcattcc       840
gatgtgattg atagtcagga actttccaaa gtcagccgtg aattccacag ccatgaattt       900
cacagccatg aagatatgct ggttgtagac cccaaaagta aggaagaaga taaacacctg       960
aaatttcgta tttctcatga attagatagt gcatcttctg aggtcaatta aaaggagaaa      1020
aaatacaatt tctcactttg catttagtca aaagaaaaaa tgctttatag caaaatgaaa      1080
gagaacatga aatgctcttt ctcagtttat tggttgaatg tgtatctatt tgagtctgga      1140
```

-continued

```
aataactaat gtgtttgata attagtttag tttgtggctt catggaaact ccctgtaaac   1200
taaaagcttc agggttatgt ctatgttcat tctatagaag aaatgcaaac tatcactgta   1260
ttttaatatt tgttattctc tcatgaatag aaatttatgt agaagcaaac aaaatacttt   1320
tacccactta aaaagagaat ataacatttt atgtcactat aatcttttgt tttttaagtt   1380
agtgtatatt tgttgtgat tatcttttg tggtgtgaat aa                       1422
```

<210> SEQ ID NO 16
<211> LENGTH: 1473
<212> TYPE: DNA
<213> ORGANISM: Rattus Norvegicus
<220> FEATURE:
<221> NAME/KEY: CDS
<222> LOCATION: (80)..(1030)

<400> SEQUENCE: 16

```
gcaagcctca gcatccttgg ctttgcagtc tcctgcggca agcattctcg aggaagccag    60
ccaaggacca actacaaacc atg aga ctg gca gtg gtt tgc ctt tgc ctg ttc   112
                      Met Arg Leu Ala Val Val Cys Leu Cys Leu Phe
                       1               5                  10 ggc ctt gcc tcc tgt ctc ccg gtg aaa gtg gct gag ttt ggc agc tca    160
Gly Leu Ala Ser Cys Leu Pro Val Lys Val Ala Glu Phe Gly Ser Ser
         15                  20                  25 gag gag aag gcg cat tac agc aaa cac tca gat gct gta gcc act tgg    208
Glu Glu Lys Ala His Tyr Ser Lys His Ser Asp Ala Val Ala Thr Trp
     30                  35                  40 ctg aag cct gac cca tct cag aag cag aat ctt cta gcc cca cag aat    256
Leu Lys Pro Asp Pro Ser Gln Lys Gln Asn Leu Leu Ala Pro Gln Asn
 45                  50                  55 tct gtg tcc tct gaa gaa acg gat gac ttt aag caa gaa act ctt cca    304
Ser Val Ser Ser Glu Glu Thr Asp Asp Phe Lys Gln Glu Thr Leu Pro
60                  65                  70                  75 agc aac tcc aat gaa agc cat gac cac atg gac gat gat gac gac gac    352
Ser Asn Ser Asn Glu Ser His Asp His Met Asp Asp Asp Asp Asp Asp
                 80                  85                  90 gat gac gac gga gac cat gca gag agc gag gat tct gtg aac tcg gat    400
Asp Asp Asp Gly Asp His Ala Glu Ser Glu Asp Ser Val Asn Ser Asp
             95                 100                 105 gaa tct gac gaa tct cac cat tcc gat gaa tct gat gag tcc ttc act    448
Glu Ser Asp Glu Ser His His Ser Asp Glu Ser Asp Glu Ser Phe Thr
        110                 115                 120 gcc agc aca caa gca gac gtt ttg act cca atc gcc ccc aca gtc gat    496
Ala Ser Thr Gln Ala Asp Val Leu Thr Pro Ile Ala Pro Thr Val Asp
    125                 130                 135 gtc cct gac ggc cga ggt gat agc ttg gct tac gga ctg agg tca aag    544
Val Pro Asp Gly Arg Gly Asp Ser Leu Ala Tyr Gly Leu Arg Ser Lys
140                 145                 150                 155 tcc agg agt ttc cct gtt tct gat gaa cag tat ccc gat gcc aca gat    592
Ser Arg Ser Phe Pro Val Ser Asp Glu Gln Tyr Pro Asp Ala Thr Asp
                160                 165                 170 gag gac ctc acc tcc cgc atg aag agc cag gag tcc gat gag gct atc    640
Glu Asp Leu Thr Ser Arg Met Lys Ser Gln Glu Ser Asp Glu Ala Ile
            175                 180                 185 aag gtc atc cca gtt gcc cag cgt ctg agc gtg ccc tct gat cag gac    688
Lys Val Ile Pro Val Ala Gln Arg Leu Ser Val Pro Ser Asp Gln Asp
        190                 195                 200 agc aac ggg aag acc agc cat gag tca agt cag ctg gat gaa cca agc    736
Ser Asn Gly Lys Thr Ser His Glu Ser Ser Gln Leu Asp Glu Pro Ser
    205                 210                 215
```

-continued

```
gtg gaa aca cac agc ctg gag cag tcc aag gag tat aag cag agg gcc      784
Val Glu Thr His Ser Leu Glu Gln Ser Lys Glu Tyr Lys Gln Arg Ala
220                 225                 230                 235 agc cac gag agc act gag cag tcg gat gcg atc gat agt gcc gag aag      832
Ser His Glu Ser Thr Glu Gln Ser Asp Ala Ile Asp Ser Ala Glu Lys
                240                 245                 250 ccg gat gca atc gat agt gca gag cgg tcg gat gct atc gac agt cag      880
Pro Asp Ala Ile Asp Ser Ala Glu Arg Ser Asp Ala Ile Asp Ser Gln
                255                 260                 265 gcg agt tcc aaa gcc agc ctg gaa cat cag agc cac gag ttt cac agc      928
Ala Ser Ser Lys Ala Ser Leu Glu His Gln Ser His Glu Phe His Ser
            270                 275                 280 cat gag gac aag cta gtc cta gac cct aag agt aag gaa gat gat agg      976
His Glu Asp Lys Leu Val Leu Asp Pro Lys Ser Lys Glu Asp Asp Arg
        285                 290                 295 tat ctg aaa ttc cgc att tct cat gaa tta gag agt tca tct tct gag     1024
Tyr Leu Lys Phe Arg Ile Ser His Glu Leu Glu Ser Ser Ser Ser Glu
300                 305                 310                 315 gtc aat taaagaagag gcaaaaccac agttccttac tttgctttaa ataaaacaaa      1080
Val Asn aagtaaattc caacaagcag gaatactaac tgcttgtttc tcagttcagt ggatacatgt   1140
atgtggacaa agaaatagat agtgttttgg gccctgagct tagttcgttg tttcatgcag   1200
acaccactgt aacctagaag tttcagcatt tcgcttctgt tctttctgtg caagaaatgc   1260
aaatggccac tgcattttaa tgattgctat tcttttatga ataaaatgta tgtagaggca   1320
ggcaaactta caggaacagc aaaattaaaa gagaaactat aatagtctgt gtcactataa   1380
tcttttggtt ttataattag tgtatatttt gttgtgatta ttttttgttgg tgtgaataaa  1440 tcttgtatct tgaatgtaaa aaaaaaaaaa aaa                                1473
```

<210> SEQ ID NO 17
<211> LENGTH: 317
<212> TYPE: PRT
<213> ORGANISM: Rattus Norvegicus

<400> SEQUENCE: 17

```
Met Arg Leu Ala Val Val Cys Leu Cys Leu Phe Gly Leu Ala Ser Cys
1               5                   10                  15

Leu Pro Val Lys Val Ala Glu Phe Gly Ser Ser Glu Glu Lys Ala His
            20                  25                  30

Tyr Ser Lys His Ser Asp Ala Val Ala Thr Trp Leu Lys Pro Asp Pro
        35                  40                  45

Ser Gln Lys Gln Asn Leu Leu Ala Pro Gln Asn Ser Val Ser Ser Glu
    50                  55                  60

Glu Thr Asp Asp Phe Lys Gln Glu Thr Leu Pro Ser Asn Ser Asn Glu
65                  70                  75                  80

Ser His Asp His Met Asp Asp Asp Asp Asp Asp Asp Asp Gly Asp
                85                  90                  95

His Ala Glu Ser Glu Asp Ser Val Asn Ser Asp Glu Ser Asp Glu Ser
            100                 105                 110

His His Ser Asp Glu Ser Asp Glu Ser Phe Thr Ala Ser Thr Gln Ala
        115                 120                 125

Asp Val Leu Thr Pro Ile Ala Pro Thr Val Asp Val Pro Asp Gly Arg
    130                 135                 140

Gly Asp Ser Leu Ala Tyr Gly Leu Arg Ser Lys Ser Arg Ser Phe Pro
145                 150                 155                 160
```

-continued

```
Val Ser Asp Glu Gln Tyr Pro Asp Ala Thr Asp Glu Asp Leu Thr Ser
            165                 170                 175

Arg Met Lys Ser Gln Glu Ser Asp Glu Ala Ile Lys Val Ile Pro Val
            180                 185                 190

Ala Gln Arg Leu Ser Val Pro Ser Asp Gln Asp Ser Asn Gly Lys Thr
            195                 200                 205

Ser His Glu Ser Ser Gln Leu Asp Glu Pro Ser Val Glu Thr His Ser
            210                 215                 220

Leu Glu Gln Ser Lys Glu Tyr Lys Gln Arg Ala Ser His Glu Ser Thr
225                 230                 235                 240

Glu Gln Ser Asp Ala Ile Asp Ser Ala Glu Lys Pro Asp Ala Ile Asp
            245                 250                 255

Ser Ala Glu Arg Ser Asp Ala Ile Asp Ser Gln Ala Ser Ser Lys Ala
            260                 265                 270

Ser Leu Glu His Gln Ser His Glu Phe His Ser His Glu Asp Lys Leu
            275                 280                 285

Val Leu Asp Pro Lys Ser Lys Glu Asp Asp Arg Tyr Leu Lys Phe Arg
            290                 295                 300

Ile Ser His Glu Leu Glu Ser Ser Ser Glu Val Asn
305                 310                 315

<210> SEQ ID NO 18
<211> LENGTH: 16
<212> TYPE: PRT
<213> ORGANISM: Artificial Sequence
<220> FEATURE:
<223> OTHER INFORMATION: Synthetic

<400> SEQUENCE: 18

Asp Pro Lys Ser Lys Glu Asp Asp Arg Tyr Leu Lys Phe Arg Ile Ser
1               5                   10                  15
```